(12) United States Patent
Charbonnet et al.

(10) Patent No.: US 8,735,142 B2
(45) Date of Patent: May 27, 2014

(54) SYSTEMS AND METHODS FOR IMMUNOSORBENT ASSAYS FOR SINGLE AND MULTIPLE ANALYTES

(75) Inventors: Derrick Charbonnet, Ocean Springs, MS (US); Norman Scott Evans, Arlington, TX (US)

(73) Assignee: Chipotle Business Group, Inc., Arlington, TX (US)

( * ) Notice: Subject to any disclaimer, the term of this patent is extended or adjusted under 35 U.S.C. 154(b) by 269 days.

(21) Appl. No.: 12/848,983

(22) Filed: Aug. 2, 2010

(65) Prior Publication Data

US 2011/0034340 A1 Feb. 10, 2011

Related U.S. Application Data

(63) Continuation-in-part of application No. 11/506,178, filed on Aug. 16, 2006, now Pat. No. 7,767,404.

(60) Provisional application No. 60/708,459, filed on Aug. 16, 2005, provisional application No. 60/708,576, filed on Aug. 16, 2005, provisional application No. 60/709,268, filed on Aug. 18, 2005.

(51) Int. Cl.
*C12M 3/00* (2006.01)

(52) U.S. Cl.
USPC ........................................................ 435/287.2

(58) Field of Classification Search
None
See application file for complete search history.

(56) References Cited

U.S. PATENT DOCUMENTS

| | | | |
|---|---|---|---|
| 5,270,164 A * | 12/1993 | Anderson et al. | 435/6.14 |
| 5,281,540 A | 1/1994 | Merkh et al. | |
| 5,281,541 A | 1/1994 | Saito et al. | |
| 6,027,946 A | 2/2000 | Weitschies et al. | |
| 6,388,788 B1 * | 5/2002 | Harris et al. | 359/196.1 |
| 6,730,521 B1 | 5/2004 | Cassells | |
| 7,494,776 B2 | 2/2009 | Wallace et al. | |
| 8,093,067 B2 * | 1/2012 | Barbreau et al. | 436/526 |
| 2003/0186214 A1 * | 10/2003 | Yan et al. | 435/4 |
| 2004/0022677 A1 * | 2/2004 | Wohlstadter et al. | 422/52 |
| 2005/0014171 A1 * | 1/2005 | Fraser et al. | 435/6 |
| 2005/0112634 A1 * | 5/2005 | Woudenberg et al. | 435/6 |
| 2005/0124008 A1 | 6/2005 | Kauvar | |
| 2006/0057635 A1 | 3/2006 | Mansson et al. | |
| 2006/0166296 A1 | 7/2006 | Nishii et al. | |
| 2007/0020713 A1 * | 1/2007 | Saini et al. | 435/7.92 |
| 2007/0292966 A1 | 12/2007 | Prickett et al. | |

FOREIGN PATENT DOCUMENTS

EP 0351857 * 7/1989 .......... G01N 33/553

* cited by examiner

*Primary Examiner* — Ann Lam
(74) *Attorney, Agent, or Firm* — Kammer Browning PLLC

(57) ABSTRACT

The present invention discloses systems and methods for minimizing or eliminating steps in immunosorbent assays for single and multiple analytes by eliminating both the need to attach target molecules to the test well and the need to remove unbound antibodies through rinsing. The immunosorbent assay (ISA) is utilized for a single analyte or target and includes the step of mixing the immunologic molecules with the sample and detection. The present invention further discloses an immunosorbent assay for multiple analytes (ISAMA) for testing a plurality of analytes or targets in a single well using a modified ISA test wherein different tags are attached to different antibody pairs. Alternate embodiments use multiple types of scavenger antigens with corresponding elimination of the need for scavenger antibodies. The present invention discloses various types of test wells for the rapid and simultaneous testing of fluids for a plurality of components and a methodology for a continuous immunosorbent assay. Also disclosed is a method for immunosorbent assay of micro-organisms to determine serotype.

16 Claims, 25 Drawing Sheets

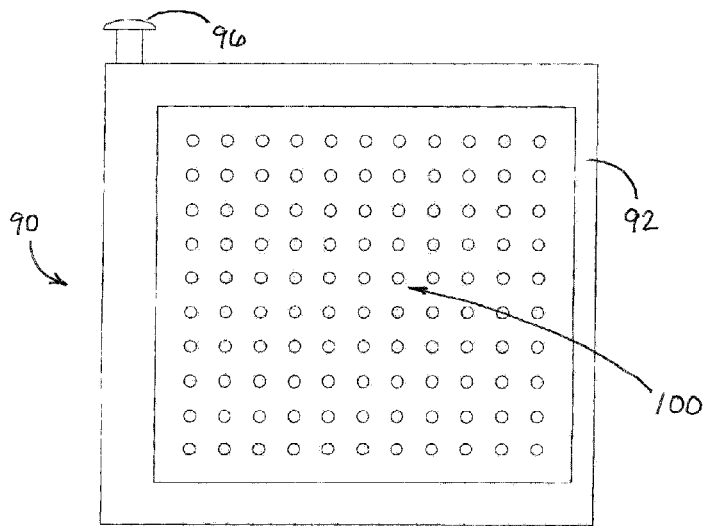
Fig. 22
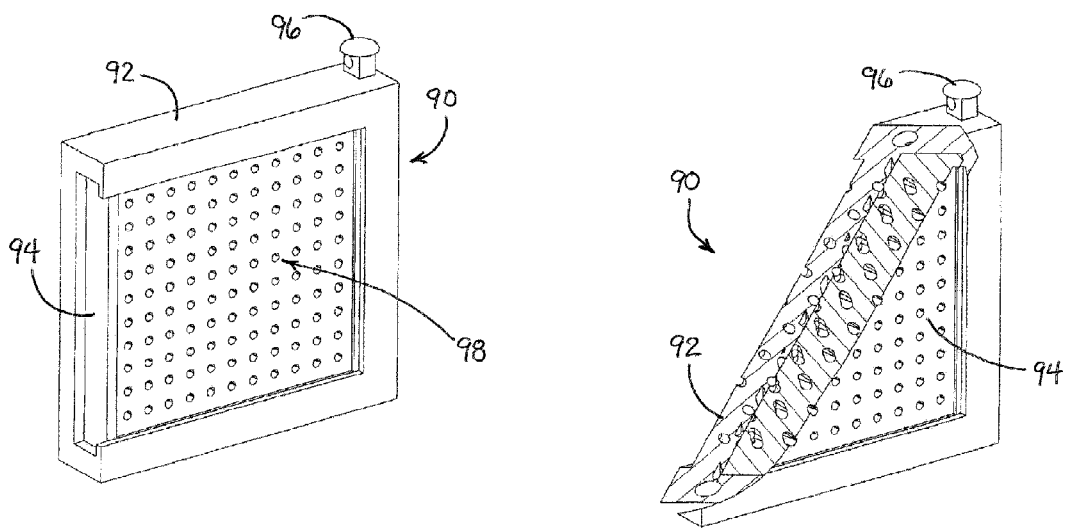
Fig. 23A
Fig. 23B

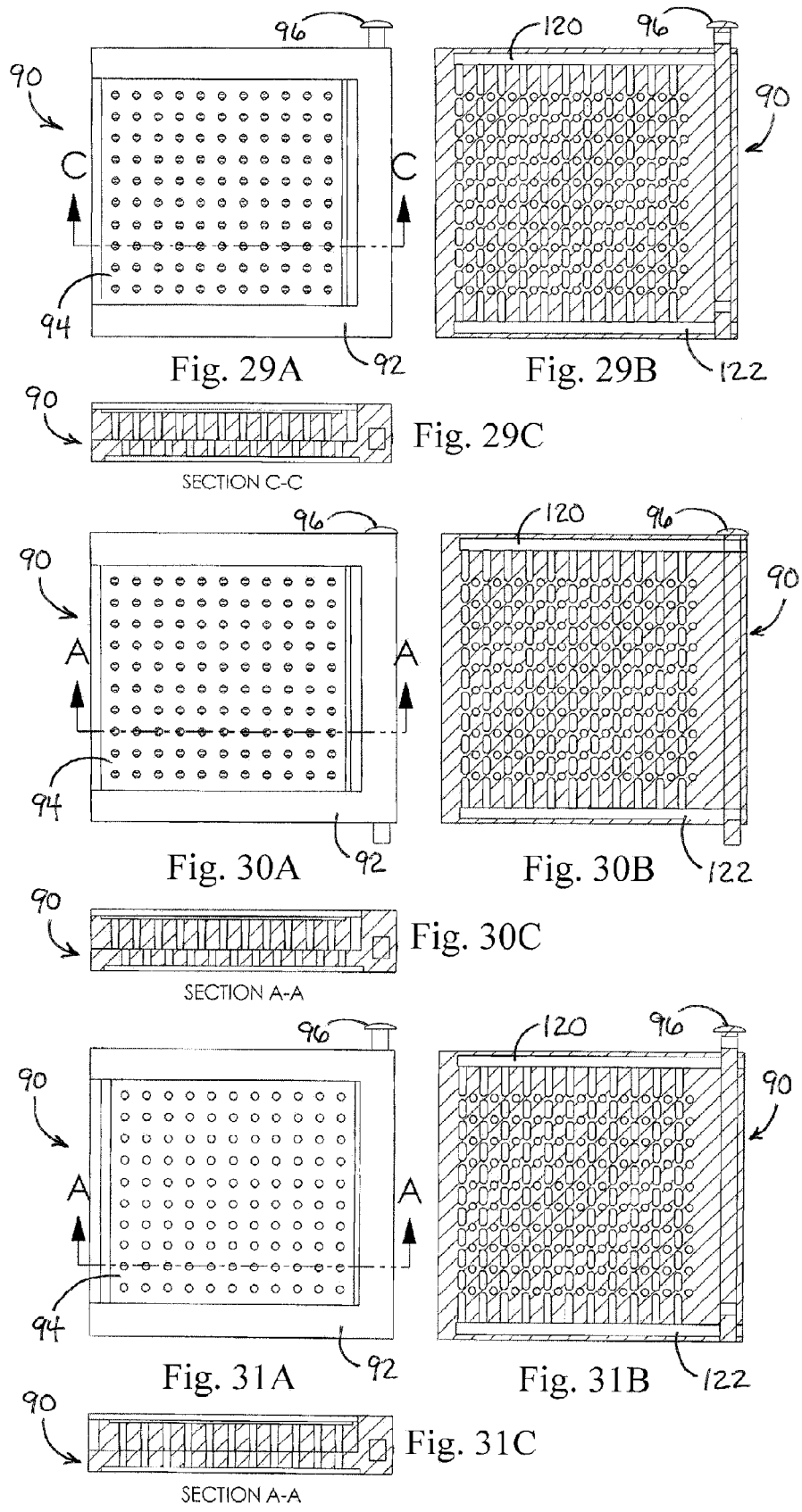

SYSTEMS AND METHODS FOR IMMUNOSORBENT ASSAYS FOR SINGLE AND MULTIPLE ANALYTES

CROSS REFERENCE TO CORRESPONDING APPLICATIONS

This application claims the benefit under 35 USC §120 of co-pending U.S. patent application Ser. No. 11/506,178 filed Aug. 16, 2006, which further claims the benefit under 35 USC §119(e) of U.S. Provisional Patent Application No. 60/708,459 filed Aug. 16, 2005; U.S. Provisional Application No. 60/708,576 filed Aug. 16, 2005; and U.S. Provisional Application No. 60/709,268 filed Aug. 18, 2005, the full disclosures of which are incorporated herein by reference.

BACKGROUND OF THE INVENTION

A vast number of biomolecules and biological entities (such as proteins and other complex molecules, and bacteria, fungal cells and other cell types) can be detected using immunologic techniques. Common among these tests, and well-known in the art, are ELISA (Enzyme-Linked ImmunoSorbent Assay) tests. Typically an ELISA test's target (the antigen) has molecular properties for which binding domains of antibodies have affinity.

Antibodies are molecules that "fit" and bind to the antigen; the binding can be strong or weak. In order to identify those biomolecules and biological entities that are bound by specific antibodies, a tag (in this case, an enzyme) is typically attached to the antibodies. These tags react with additional chemical markers that, after enzymatic catalysis, fluoresce or cause the solution to change color. Other immunologic tests use radioactive tags (e.g., radio-immuno assay, or RIA, tests).

All of these immunologic tests require multiple steps. In an ELISA test, for example, a first step is to attach target entities to a test well. A second step is to introduce a fluid containing tagged antibodies into the well. The tagged antibodies then bind with considerable specificity to matching antigens (and less so, or not at all, to the other entities that may be present in the well). After fluid is removed, the test well is rinsed to remove unbound antibodies (if a detection step is prematurely implemented before rinsing, all antibodies, whether tightly bound to antigen or unbound, may potentially be detected). Finally, the well is refilled with a neutral fluid and marker chemicals are added. A detection step is then implemented, and the presence or amount of antigen is determined from a color change or florescence measurement. A reliable and efficient means of minimizing or eliminating steps in immunosorbent assays is needed.

Testing of a liquid sample often requires manually adding a liquid reagent to the liquid sample followed by manually mixing the liquid sample and the added liquid reagent. For example, in order to test a liquid sample, a researcher may add, through the use of a micropipette, a liquid reagent to an aliquot of the liquid sample in a microtube.

The researcher may then need to mix the liquid sample with the added liquid reagent by further repetitively drawing up and expelling the mixture from the micropipette into the microtube. User variability (e.g., that may result from fatigue on the part of the researcher) or method variability introduced by relying on such micropipette-based mixing may adversely affect the reliability of subsequent measurements (e.g., colorimetric readings of chemical reactions in the liquid mixture).

The mixing of liquids is accomplished in some methods of high throughput screening (e.g., utilizing standard 96-well, 384-well, 1536-well or 3456-well plates) through automated additions of liquids across rows of wells within plates. These high throughput screening methods, however, generally require extensive electromechanical equipment and computer programming support for implementation. A generally simpler system for effecting the simultaneous mixing of a plurality of liquids is often needed.

SUMMARY OF THE INVENTION

The present invention provides a reliable and efficient means of minimizing or eliminating steps in immunosorbent assays. The method of the present invention is a generally simpler system for effecting the simultaneous mixing of a plurality of liquids. The present invention enables testing for any reasonably clear fluid. The test substances need not be floating but rather may be bound, attached, or part of a surface as long as the surface can be submerged in the fluid. A wide variety of scavenger antigens may be utilized as long as the antibody concerned binds to the scavenger antigen no better than it does to the target.

Some of the embodiments of the present invention are directed to the analysis of a single analyte in an immunosorbent assay, while other embodiments of the present invention are directed to the analysis of multiple analytes or targets per well in an immunosorbent assay. All of the embodiments of the present invention provide means of minimizing or eliminating steps in immunosorbent assays. The core steps of mixing the immunologic molecules with the sample and then accomplishing detection remain, thus resulting in a simpler ImmunoSorbent Assay (ISA). This reduction in steps is accomplished primarily by eliminating the need for two steps: 1) attaching target molecules to the well, and 2) removing unbound antibodies through rinsing.

The embodiments of the invention directed to a test for a plurality of analytes or targets in a single well use a modified ISA test, thus resulting in ImmunoSorbent Assay for Multiple Analytes (ISAMA). A primary means of detecting multiple analytes (or multiple targets) in embodiments of ISAMA is by attaching different fluorescent tags (e.g., tags that fluoresce at different wavelengths of light) to different antibody pairs.

The present invention further includes various types of test vessels including single wells, multiple wells, cassettes having multi-part test wells, and various structures separate from a well, including continuous flow devices. Such variations allow for the rapid and simultaneous testing of fluids for a plurality of components. Also disclosed is a method for immunosorbent assay of micro-organisms. Embodiments of this invention utilize colorimetric reactions of reagents in a unique way for the easy performance of such testing. This summary of the invention is not intended to represent each embodiment or every aspect of the present invention.

BRIEF DESCRIPTION OF THE DRAWINGS

A more complete understanding of the systems and methods of the present invention may be obtained by reference to the following Detailed Description when taken in conjunction with the accompanying Drawings, wherein:

FIG. 22 is a flat-on broad side view of this second embodiment of a cassette for testing fluids;

FIGS. 23A and 23B diagram a diagonal cut-away view of this second embodiment of a cassette for testing fluids;

FIGS. 29A-29C diagram this second embodiment of a cassette for testing fluids in a closed, ready-to-use position;

FIGS. 30A-30C diagram this second embodiment of a cassette for testing fluids in a sample-taking position;

FIGS. 31A-31C diagram this second embodiment of a cassette for testing fluids in an analysis position;

DETAILED DESCRIPTION OF THE PREFERRED EMBODIMENTS

Figure 1:
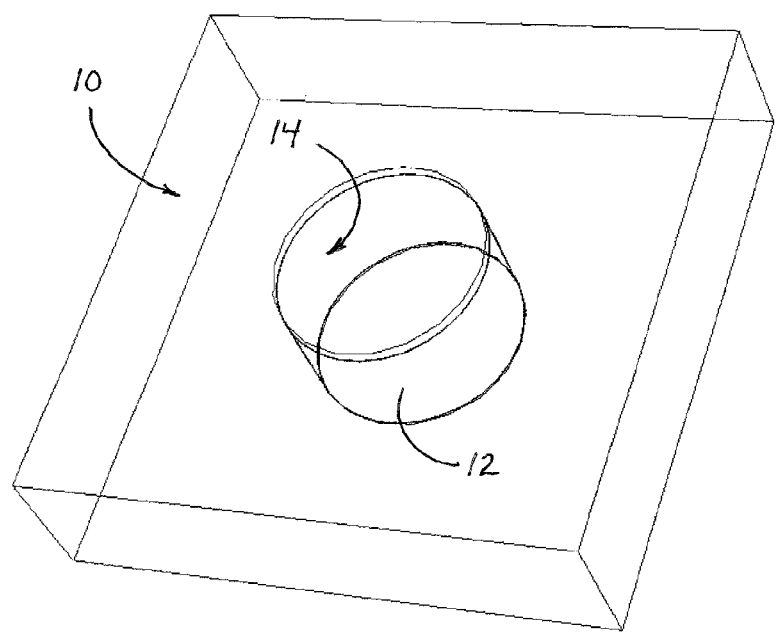
FIG. 1 is a test well with scavenger antigens.

As summarized above, the present invention is directed to systems and methods for immunosorbent assay for single and multiple analytes. The present invention includes the following components: an immunosorbent assay for a single analyte, an immunosorbent assay for multiple analytes, and various vessel structures for testing fluids and methods of use in immunosorbent assays.

Immunosorbent Assay for a Single Analyte

Embodiments of this invention make use of florescent tags (or other tags that react specifically to light or other electromagnetic energy). For example, instead of target entities being bound to the well, a second antigen (the "scavenger antigen") that is similar to the antigen in question is obtained or prepared and bound to the well. In embodiments of the invention, this scavenger antigen is bound only to the walls of the well, not the bottom. In other embodiments, scavenger antigens may be bound only to the bottom of a well (and the detection light beam shone through clear well sides so as to limit or avoid illumination of the well bottom). The antibodies bind to scavenger antigen but with less affinity or avidity than to target molecules. In some embodiments, the number of scavenger antigens considerably exceeds the number of antibodies.

In other configurations of the invention, the diameter of the well is larger than the diameter of the light beam used for detection. After the antibody solution is added to the well, the target solution is added, and the well is agitated. The antibodies present bind to either the targets, which are largely suspended in solution, or the scavenger antigens on the well walls. In further aspects, there must be enough time and agitation to ensure that all the antibodies are bound either to the targets or the scavenger antigens.

In further embodiments, a detection light beam, either a laser or another tightly focused beam, is then shone through the well. In some embodiments, the walls of the well are out of the path of the detection light or the walls are shaped in such a way as to cast shadows in order to prevent or minimize the detection beam's striking the tagged antibodies bound to scavenger antigen on the walls. When the detection light beam shines into the well, it strikes the targets suspended in solution within the well and not the antibodies bound to the walls.

Thus in these embodiments, only the florescence from the antibodies bound to targets is detected. In addition to being shone through the well, the beam can be absorbed or reflected off the well bottom in other embodiments. The emissions from the tagged antibodies can be detected from the top, bottom, or any convenient direction in various embodiments.

In another embodiment, the scavenger antigens are attached to items or carriers that float or remain suspended in the fluid of the well. These items or carriers have holes within which shadow areas are created and within which the scavenger antigens attach.

In another embodiment, wells having perpendicular ridges along their side wall are utilized, and scavenger antigen is attached along the inside of these ridges. The ridges can shadow tagged antibodies bound to scavenger antigen and prevent light emissions from these tagged antibodies from otherwise contaminating detection measurements.

In another embodiment, radioactive tags are used with wells that have sufficient shadowing elements to prevent stray radiation from disrupting detection of radioactivity from tagged antibodies bound to target molecules.

It is also possible to have two (or more) types of antibodies each with a different type of tag and two (or more) types of scavenger antigens fixed to the well, essentially running two different single analytes, i.e., two ISA's, at the same time.

It is to be understood that the measurement used to quantify the tagged antibodies present (i.e., not bound to a scavenger antigen) could be direct as described herein, or differential, wherein measurement of the tagged antibodies drawn to the scavenger antigens is made.

In another embodiment, the immunosorbent assay for a single analyte is conducted using bound (conjugated) antibody pairs, i.e., primary and scavenger. This is in contrast to the primary embodiment for ISA wherein no scavenger antibody is utilized. This may be necessary in certain circumstances in which the scavenger antigen does not sufficiently attract or bind to the tagged target antibody.

Figure 2:
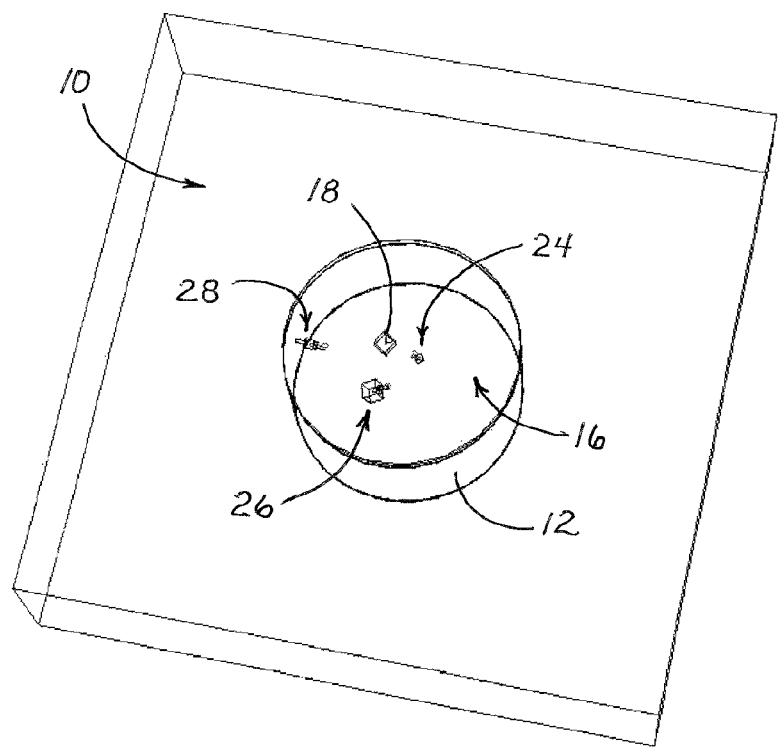
FIG. 2 is a test well with target fluid added.
Figure 3:
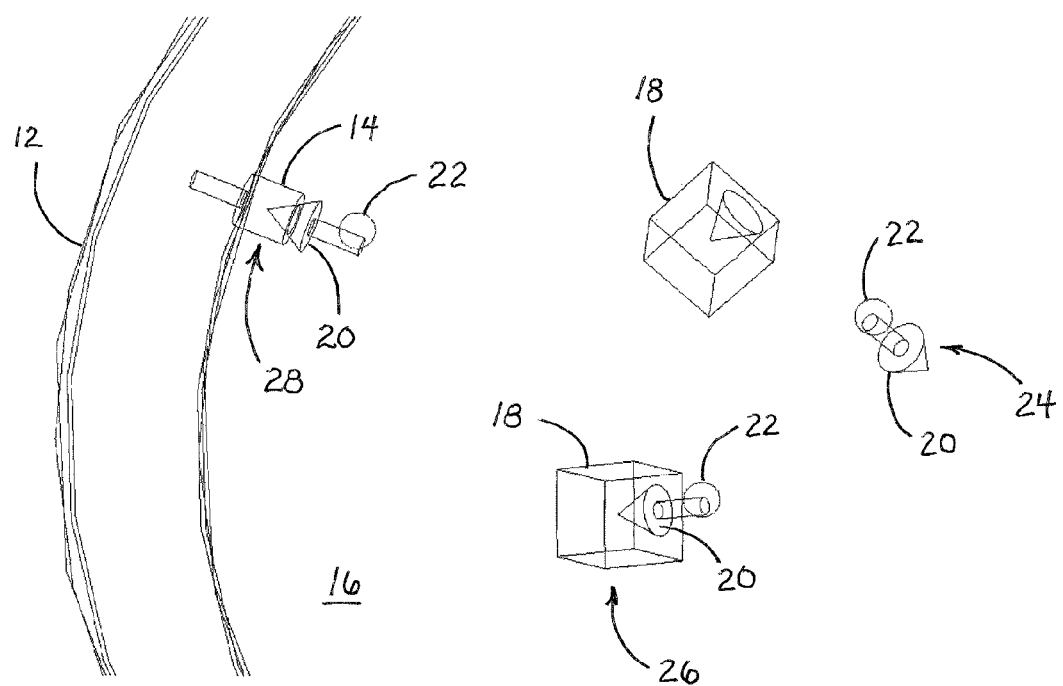
FIG. 3 is a model of antibodies (cones) and antigens (cubes: targets; cylinders: scavenger antigens)
Figure 4:
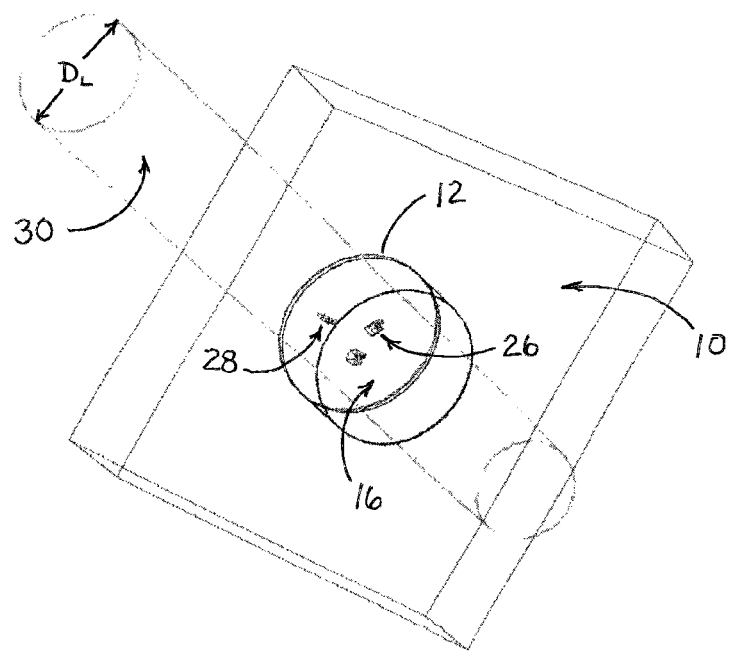
FIG. 4 is a test well through which a detection light beam passes.
Figure 5:
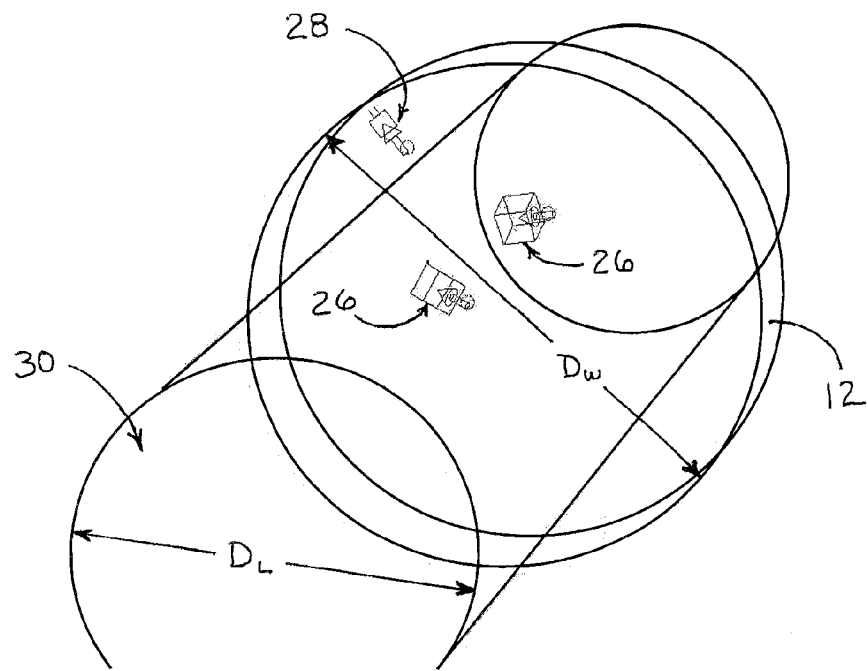
FIG. 5 illustrates a test well with a detection light detecting target antigens and not detecting scavenger antigen.
Figure 6:
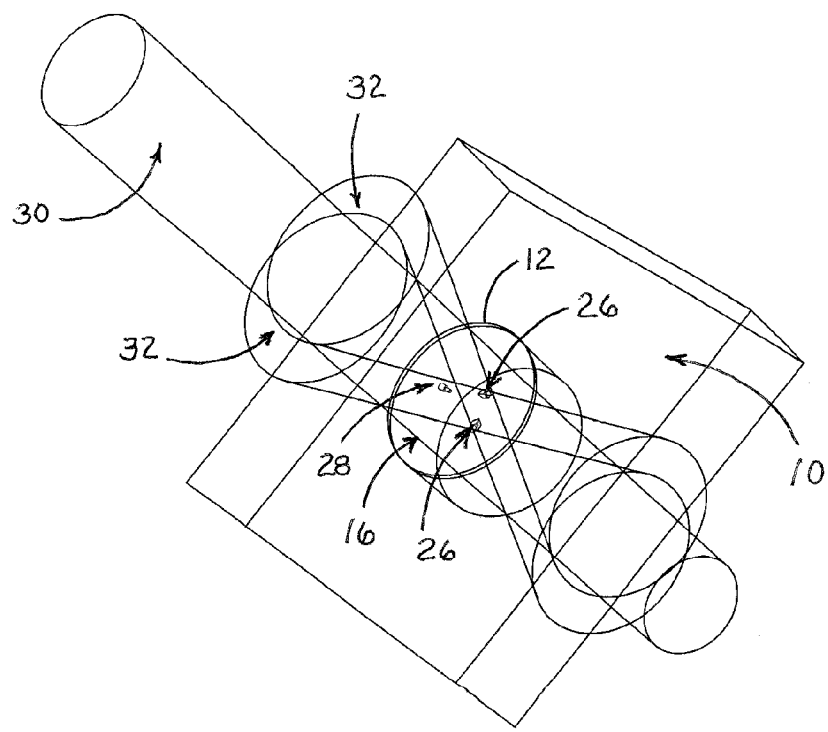
FIG. 6 illustrates a test well containing tags in solution within the well fluorescing and tags attached to scavenger antigens not fluorescing.

FIG. 1 is a test well 10 with well wall 12 and scavenger antigens 14. FIG. 2 is a test well with target fluid 16 added. Also shown in FIG. 2 are target antigen 18, antibody with tag 24, target antigen bound to antibody with tag 26, and scavenger antigen bound to antibody with tag 28. FIG. 3 is a model of antibodies (cones) 20 and antigens (cubes: targets 18; cylinders: scavenger antigens 14), and tags (spheres) 22. FIG. 4 is a test well 10 through which a detection light beam 30 passes. FIG. 5 illustrates a test well 10 of diameter with a detection light 30 of diameter detecting target antigens 18 and not detecting scavenger antigen 14. FIG. 6 illustrates a test well 10 containing target antigen bound to antibody with tag 26 in solution within the well fluorescing 32 and antibody with tag attached to scavenger antigen 28 not fluorescing. These and other embodiments include characteristics noted in Table 1.

TABLE 1

Single Analyte Methodology Features

| No. | Description of Characteristics of Embodiments |
|---|---|
| 1 | Detection is accomplished with a beam of electromagnetic energy or radiation. The beam is shielded, focused, lased, or controlled in some way so as specifically to avoid illumination of areas where scavenger antigens are located. |
| 2 | Scavenger antigen is obtained or prepared has an equal to or lower binding affinity or avidity with the antibody than the target antigen has with the antibody in order to ensure that the antibodies preferentially bind to the targets. |
| 3 | Scavenger antigen is bound to a portion of the well that is not illuminated by the detection beam but the antibody-containing test solution yet contacts that portion of the well. |
| 4 | The scavenger antigen may be bound to items floating or suspended in the well, but these items have holes, pits, etc., that shadow tagged antibodies that bind to the scavenger antigen. |
| 5 | Antibody is obtained or prepared that binds tightly to the target antigen. |
| 6 | Antibody is conjugated with a tag that fluoresces or radiates when struck by the detection beam. The resulting fluorescence or radiation is detected by devices inside or outside the well. |
| 7 | The tagged antibody is capable of being dissolved or suspended in the test fluid. |
| 8 | The detection beam can be switched on and off, and yet the signal from the tagged antibody can be detected during the off periods. |
| 9 | The detection beam can be continuous, and yet the signal from the tagged antibody can be detected as an additional signal. |
| 10 | The detection of the signal from tagged antibodies can be accomplished from a range of angles. |
| 11 | The well has lips that provide additional shadow area to shield the scavenger antigen from the detection beam. |
| 12 | The well has ridges on its walls that provide additional shadow area to shield the scavenger antigen from the detection beam. |
| 13 | The well has depressions or holes that provide additional shadow area to shield the scavenger antigen from the detection beam. |
| 14 | The well bottom does not reflect or scatter the detection beam back into the well. |
| 15 | The test fluid surface may be flat and does not act as a lens. |
| 16 | The test fluid surface may be made flat by contact with a well top. |
| 17 | The test fluid surface may be made flat by avoiding surface tension differences between the fluid and the well. |
| 18 | The test fluid surface may be made flat by filling the well exactly to the neutral fill volume between the meniscus above and below the top of the well. |

Figures 36A, 36B, 36C:
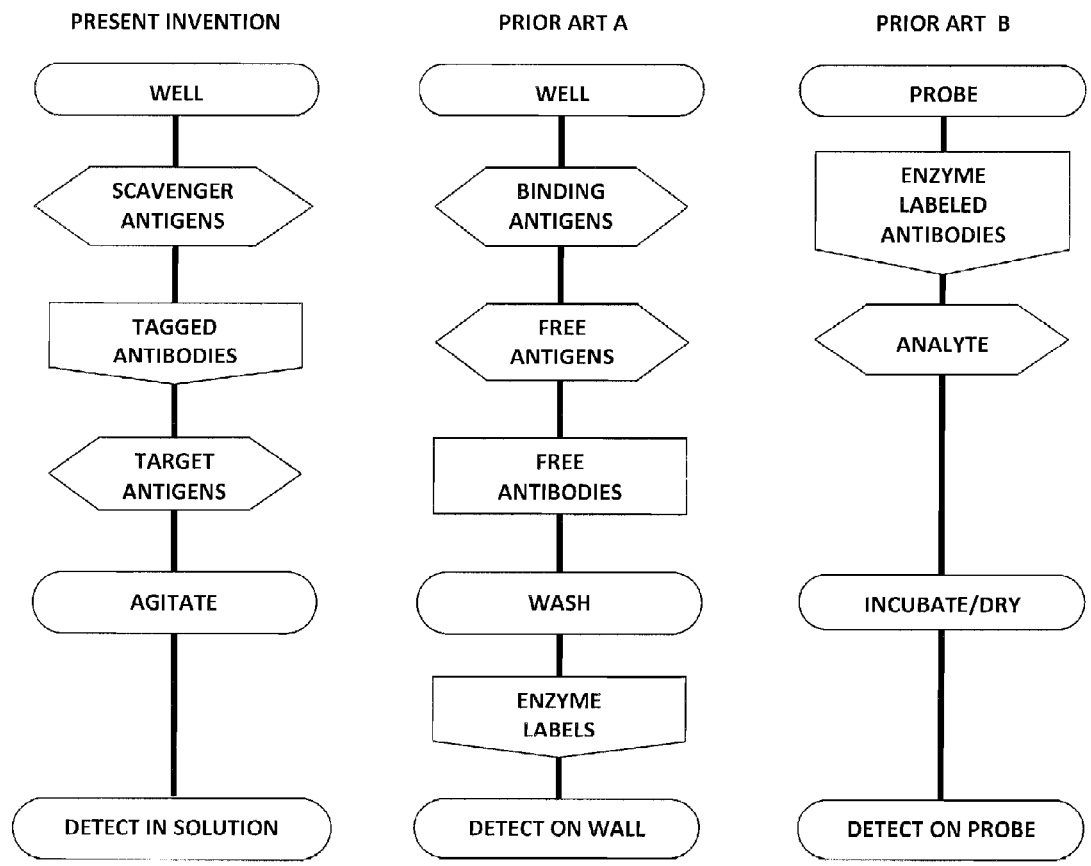
FIG. 36A is a diagram identifying the basic steps in the methodology of the present invention.
FIG. 36B is a diagram identifying the basic steps in a first method in the prior art.
FIG. 36C is a diagram identifying the basic steps in a second method in the prior art.

Examples of the prior art A and B, as shown in FIGS. 36B and 36C respectively, each carry out an assay that involves the critical step of washing a solution away and detecting tags or labels on the well wall, a probe, or a substrate. The present invention is fundamentally distinct from the prior art in that it carries out an assay without the necessity of removing the solution from the well. The detection of tags is carried out with all components added to the well remaining in the well. This is a fundamental distinction and a fundamental advantage. The use of tagged antibodies introduced into the well provides much greater ease of use, speed of detection, and efficiency in the field. As shown in FIG. 36A, one primary embodiment of the method of the present invention includes not simply the tagging of the antibodies before introduction into the well, but more importantly the elimination of two steps in the process. Agitation in the present invention occurs immediately prior to the detection step as a manner of fully dispersing the competitively bound tagged antibodies. The present invention directly measures the bound tagged antibodies/target antigens, resulting in a quick and accurate measurement of the target antigens in the sample.

Figure 37:
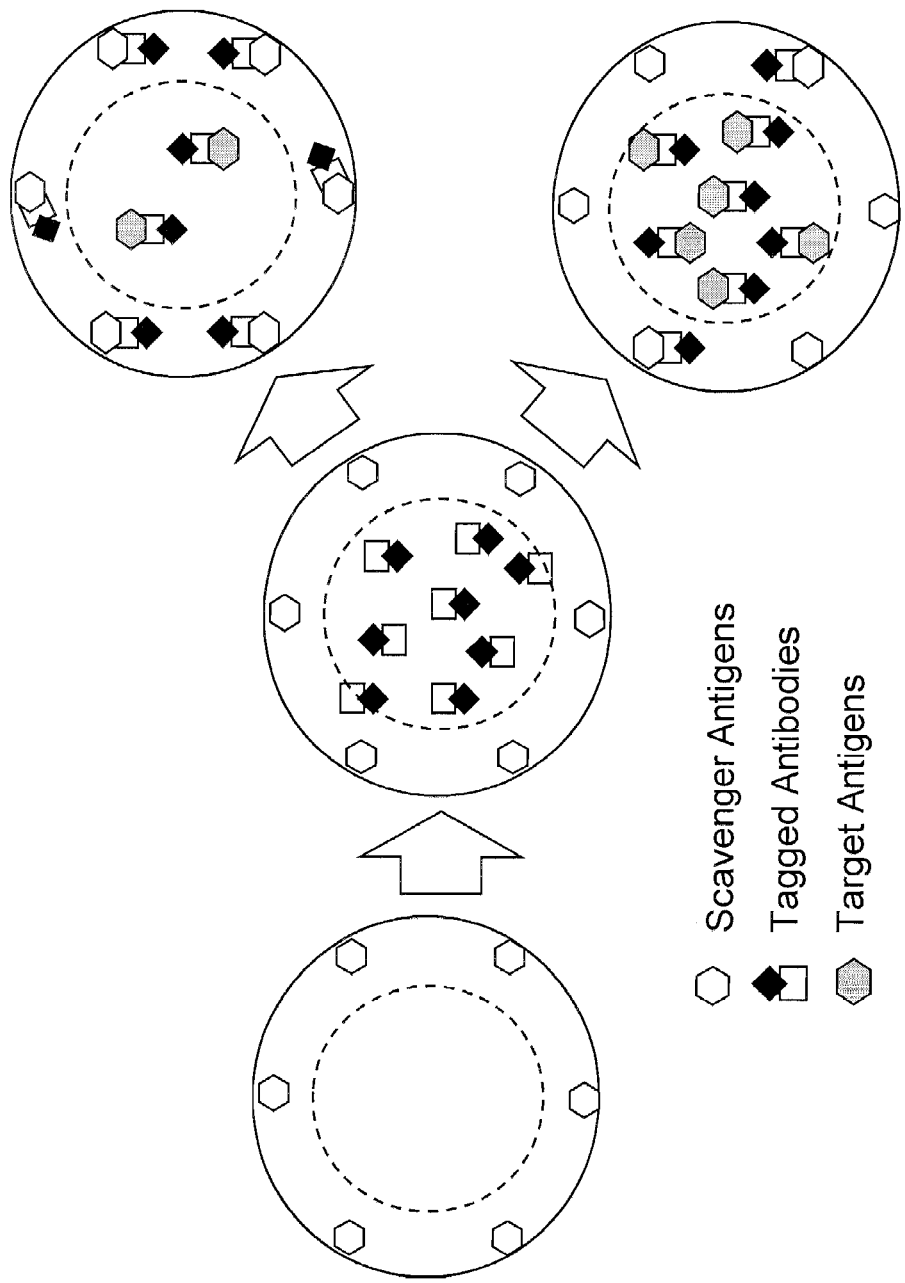
FIG. 37 is a schematic representation of the immunoassay of a single analyte of the present invention.

FIG. 37 is a schematic representation of the immunoassay of the present invention for a single analyte. The methodology is much simpler than the prior art. The present invention therefore improves upon the more complicated "lab bench" assay methods of the prior art and achieves detection in the field by utilizing a method that follows a simpler process (made possible by way of the structure of the well and the detection method). In contrast to the direct detection method of the present invention (see FIG. 37), the prior art typically utilizes an indirect method for quantifying the free antigen levels in the sample by measuring what remains after the sample has been washed from the well.

Immunosorbent Assay for Multiple Analytes

Embodiments of ISA and embodiments of ISAMA share fundamental characteristics. As in embodiments of ISA, for example, embodiments of ISAMA make use of florescent tags (or other tags that react specifically to light, other energy, or radioactivity). In embodiments of ISAMA, however, a second antibody (scavenger antibody) is obtained or prepared. Furthermore, unlike in embodiments of ISA, scavenger antigen in embodiments of ISAMA is matched to scavenger antibody but not to target antibody. Binding between scavenger antibody and scavenger antigen is generally of a lower affinity or avidity than the binding between primary antibody and target molecule in embodiments of ISAMA. Key to ISAMA is a plurality of tagged antibodies (each with an individually distinguishable tag) and a plurality of scavenger antibodies which perform just as in ISA. The result, however, allows the detector (by means of a methodology of distinguishing the tags) to count each type separately.

In embodiments of ISAMA, primary antibody and scavenger antibody are conjugated as an antibody pair (i.e., ISAMA antibody pair) and, additionally, a tag is attached to the ISAMA antibody pair. Such use of a conjugated pair permits the reduction of types of scavenger antigens to one. If conjugated pairs of antibodies are not used, then multiple types of scavenger antigens must be employed, i.e., one for each antibody/target. In embodiments of ISAMA, scavenger antigen binds to scavenger antibody but with less affinity or avidity than primary antibody binds to a target molecule or intended analyte. In preferred embodiments, many more scavenger antigens are present than ISAMA antibody pairs (i.e., pairs of primary antibody conjugated to scavenger antibody).

In embodiments of ISAMA, the scavenger antibody and the target antibody are conjugated in such a way that they both cannot or do not bind to their respective antigens at the same time.

In embodiments of ISAMA, primary antibody species or kinds are in one-to-one correspondence with species or kinds of targets or analytes for which testing is to be accomplished. That is, in embodiments of ISAMA, a primary antibody species or kind of a ISAMA antibody pair only cross-reacts or binds with high affinity or avidity to one species or kind of target or analyte. Furthermore, in embodiments of the invention, each primary antibody species or kind (e.g., of a ISAMA antibody pair) has an identifying tag (e.g., one that fluoresces at a specific wavelength, or responds to, or emits, a specific type of radiation).

As in embodiments of ISA, scavenger antigen is attached to the sides of a well in embodiments of ISAMA. Binding of scavenger antibody (e.g., of a ISAMA antibody pair) to scavenger antigen attached to a well wall is thus facilitated in embodiments of ISAMA.

In further embodiments of ISAMA, mixtures of ISAMA antibody pairs (i.e., various pairs wherein, for example, the primary antibody that is conjugated to scavenger antibody may differ for each antibody pair type) may be added to a solution within the well so that a different primary antibody type or kind of a ISAMA antibody pair mixture matches to specific types or kinds of target molecules that are added to the well. In embodiments of ISAMA, each type or kind of ISAMA antibody pair is identifiable by the type or kind of tag that is attached to the primary antibody of each ISAMA antibody pair.

In embodiments of ISAMA, when a well solution containing ISAMA antibody pairs is agitated or otherwise allowed to incubate, the various conjugated primary antibodies of the ISAMA antibody pairs bind to the various matching target molecules; all ISAMA antibody pairs that do not bind (via their conjugated primary antibody component) to targets in solution bind (via their opposite conjugated scavenger antibody component) to the scavenger antigen attached to well walls. As a result, in embodiments of ISAMA, only tagged ISAMA antibody pairs that are bound to targets remain floating or suspended in the well solution.

In further embodiments of ISAMA, a detection light beam, a laser, or another tightly focused beam, is then shone through the well. In some embodiments of ISAMA, the walls of the well are out of the path of the detection light or the walls are shaped in such a way as to cast shadows to prevent or minimize the detection beam's striking the tagged ISAMA antibody pairs bound to scavenger antigen on the walls. When the detection light beam shines into the well, it strikes the tagged ISAMA antibody pair-bound targets floating or suspended in solution within the well, but the detection light beam does not strike the tagged ISAMA antibody pairs bound to scavenger antigen that is attached to the walls.

Thus, in these embodiments of ISAMA, only the florescence from the tagged ISAMA antibody pairs bound to targets floating or suspended in solution is detected. The intensity of specific florescence wavelengths (or other characteristics used to distinguish tagged ISAMA antibody pairs that bind to a different analyte or target species or kinds) can be used to quantify the levels of analyte or other target floating or suspended in the well.

In addition to being shone through the well, the beam can be absorbed or reflected off the bottom in other embodiments of ISAMA. Emissions from the tagged ISAMA antibody pairs can be detected from the top, bottom, or any convenient direction in various embodiments.

Fluorescing radiation from tagged ISAMA antibody pairs bound to analytes or targets shines from the well to the detectors in embodiments of ISAMA; the detector has the capacity to distinguish signals that are simultaneously transmitted but that differ or vary based on the tagged ISAMA antibody pair from which a signal originated. Again, in embodiments of ISAMA, specific tagged ISAMA antibody pairs bind (via their conjugated primary antibody component) to specific target molecules. In some ISAMA embodiments, the fluorescing radiation or light shines into a spectroscopic analyzer. This device, well known in the art, spreads the light out in the manner of a prism and then uses a photosensitive device (such as a photosensitive charge-coupled device or CCD) to convert radiation spectra into electrical or digital signals specific for each of the different tags. In embodiments of ISAMA, the strength of an electrical or digital signal specific for a tag is proportional to the concentration of analyte or target suspended in the well.

In another embodiment of ISAMA, the scavenger antigens are attached to items or carners that float or remain suspended in the fluid of the well. These items or carners have holes within which shadow areas are created and within which the scavenger antigens attach.

In another embodiment of ISAMA, wells having perpendicular ridges along their side wall are utilized, and the scavenger antigen is attached along the inside of these ridges. The ridges can shadow tagged ISAMA antibody pairs bound to scavenger antigen and prevent light emissions from these tagged ISAMA antibody pairs from otherwise contaminating detection measurements.

In another embodiment, radioactive tags are used in place of, or in addition to, fluorescent tags on ISAMA antibody pairs with wells that have sufficient shadowing elements to prevent stray radiation from disrupting detection of radioactivity from tagged antibodies bound to analyte or target molecules.

Once again, it is to be understood that the measurement used to quantify the tagged antibodies present (i.e., not bound to a scavenger antigen) could be direct as described herein, or differential, wherein measurement of the tagged antibodies drawn to the scavenger antigens is made.

Figure 7:
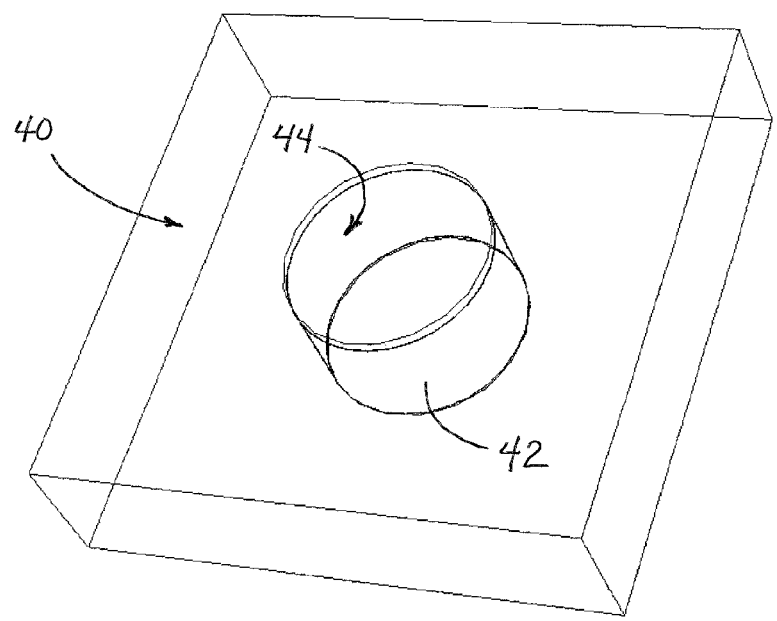
FIG. 7 is a well with scavenger antigens.
Figure 8:
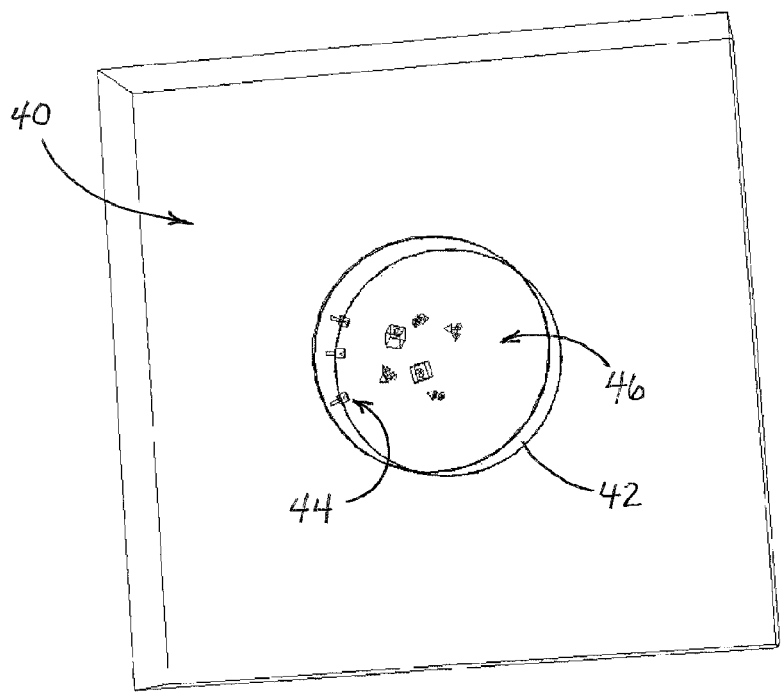
FIG. 8 is a well with target fluid added having targets and antibody pairs suspended or floating freely in the solution.
Figure 9:
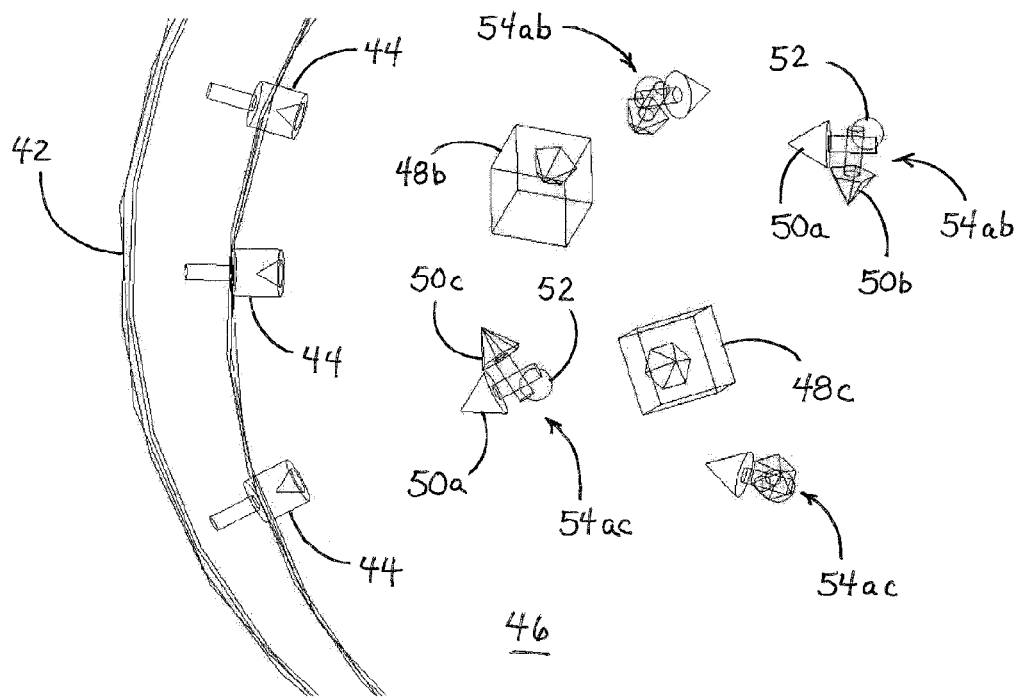
FIG. 9 is a model of ISAMA antibody pairs and antigens with two types of tagged antibody pairs and two types of targets depicted.

FIG. 7 is a test well 40 with well wall 42 and scavenger antigens (cylinders) 44. FIG. 8 is a test well 40 with target fluid 46 added having targets and antibody pairs suspended or floating freely in the solution. FIG. 9 is a model of ISAMA antibody pairs (tagged cone pairs) 54*ab* and 54*ac* and antigens (cubes: targets 48*b* and 48*c*; cylinders: scavenger antigens 44). Two types of tagged antibody pairs 54*ab* and 54*ac* and two types of targets 48*b* and 48*c* are depicted (the two types of tagged antibody pairs differ in the type of primary or target antibody that is conjugated with scavenger antibody in each tagged antibody pair). The tag (sphere) 52 is also shown. The tag used for one primary antibody may be distinguished from the tag used for a different primary antibody. FIG. 9 also depicts three types of antibodies: circular cone 50*a*, pentagon cone 50*b*, and hexagon cone 50*c*.

Figure 10:
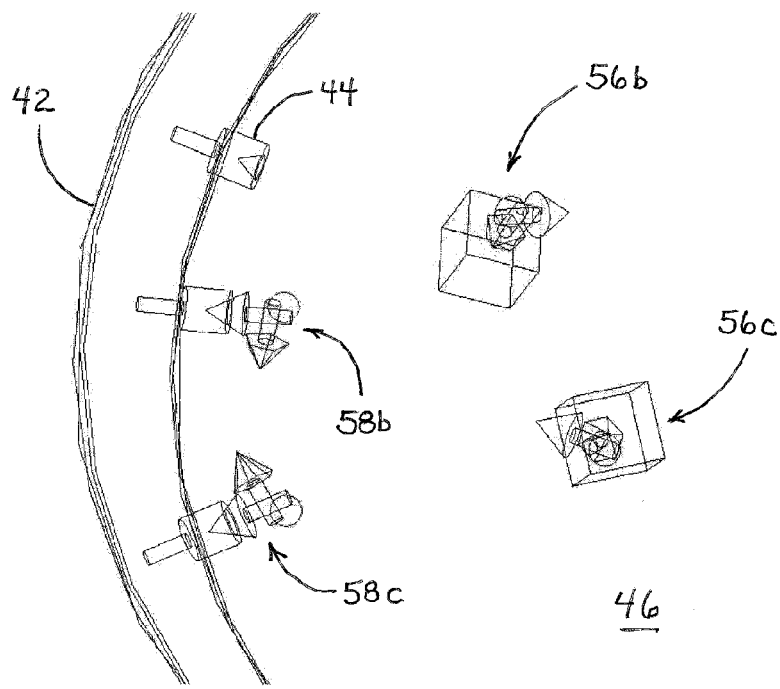
FIG. 10 illustrates four ISAMA antibody pairs: one of two ISAMA antibody pairs that is suspended in solution is bound to one type of target, and the other of two ISAMA antibody pairs that is suspended in solution is bound to another type of target; two of the four ISAMA antibody pairs are in excess and are bound to scavenger antigens attached to the well wall.

FIG. 10 illustrates four ISAMA antibody pairs (one of two ISAMA antibody pairs (56*b* and 56*c*) that is suspended in solution is bound to one type of target, and the other of two ISAMA antibody pairs that is suspended in solution is bound to another type of target; two of the four ISAMA antibody pairs (58*b* and 58*c*) are in excess and are bound to scavenger antigens attached to the well wall). Each of the two depicted targets is appropriately bound by a corresponding ISAMA antibody pair, and each of the two depicted excess ISAMA antibody pairs is bound (via its scavenger antibody) to scavenger antigen attached to the well wall. As noted for FIG. 9, the tag used for one primary antibody may be distinguished from the tag used for a different primary antibody.

Figure 11:
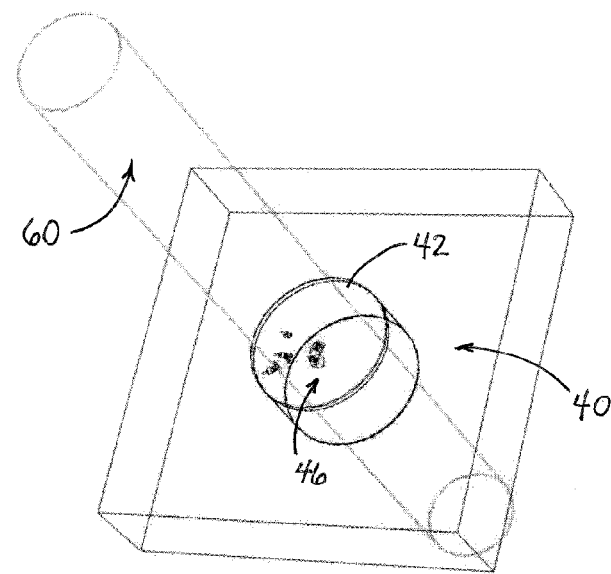
FIG. 11 is a well through which a detection light passes.
Figure 12:
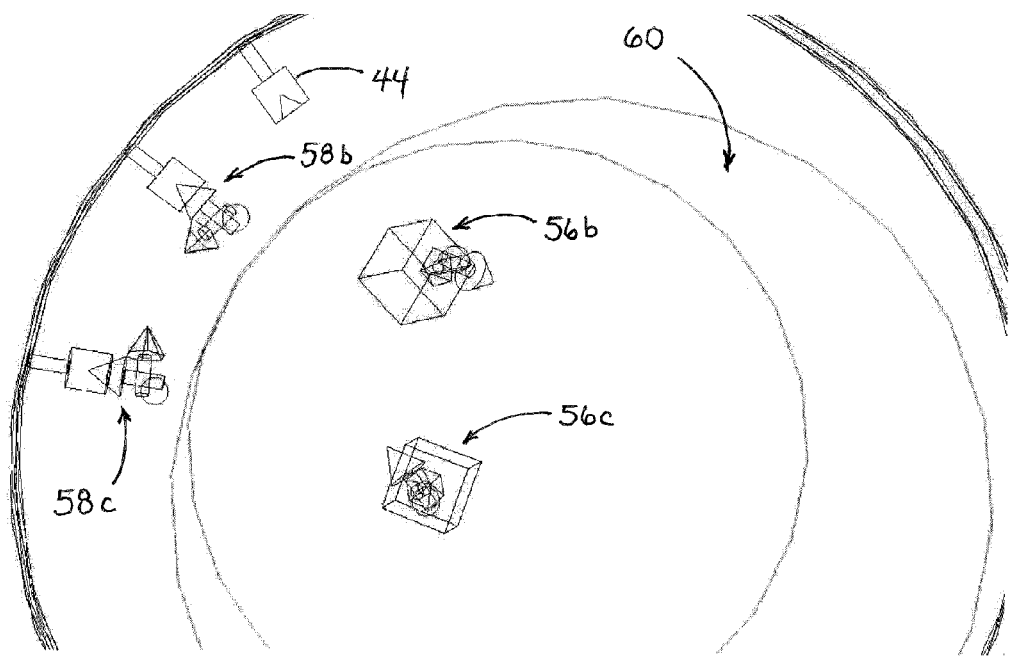
FIG. 12 illustrates detection light missing scavenger antigen.
Figure 13:
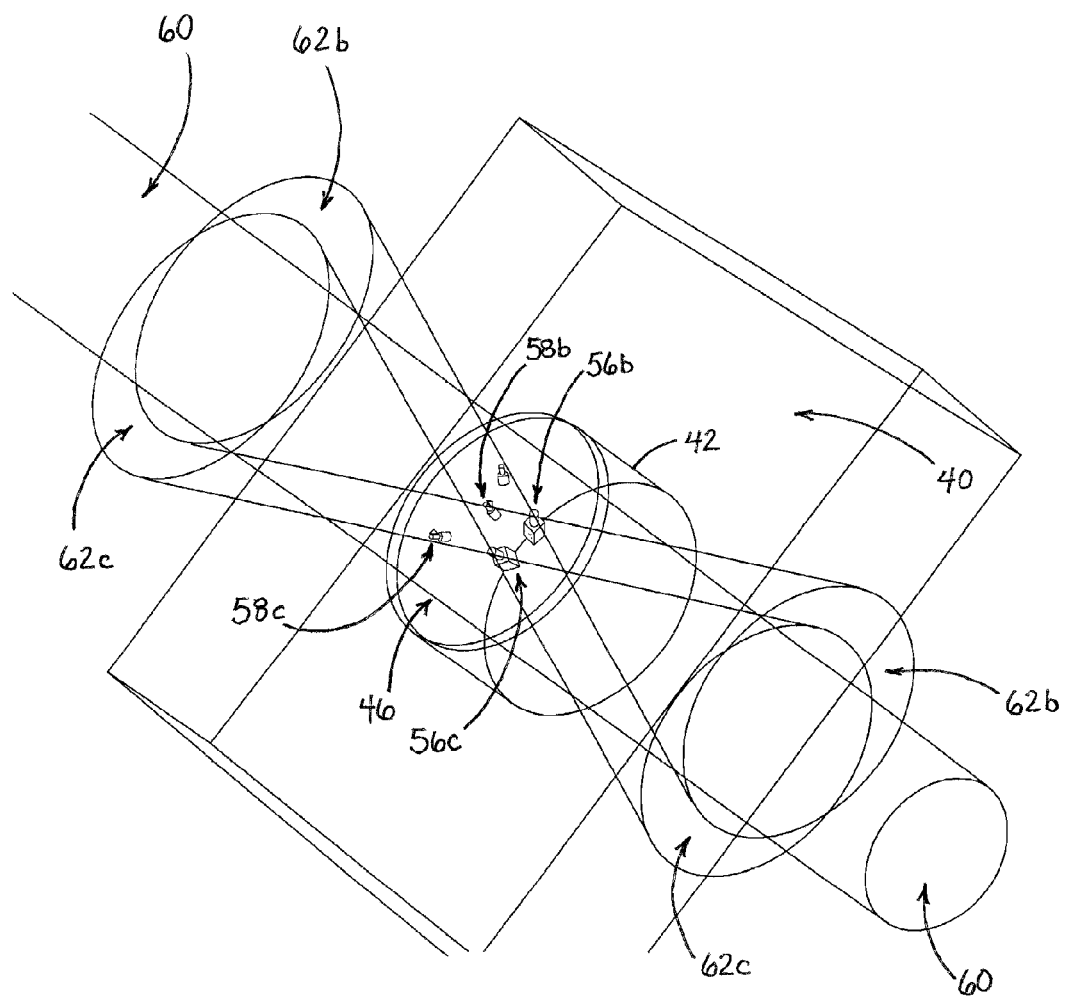
FIG. 13 illustrates that tags on ISAMA antibody pairs bound to target antigen in solution within a well fluoresce, but those tags on ISAMA antibody pairs that are bound to scavenger antigen attached to the well wall do not fluoresce.

FIG. 11 is a test well 40 through which a detection light beam 60 passes. FIG. 12 illustrates detection light beam 60 missing scavenger antigen 44 (detection light also is missing two tagged ISAMA antibody pairs bound to scavenger antigen 58*b* and 58*c*; detection light beam 60 is also illustrated as illuminating each of two tagged ISAMA antibody pairs, each of which is bound to a different target antigen 56*b* and 56*c*). FIG. 13 illustrates that tags on ISAMA antibody pairs bound to target antigen in solution within a well fluoresce 62*b* and 62*c* (each of the two different ISAMA antibody pairs fluoresces radiation of a different color), but those tags on ISAMA antibody pairs that are bound to scavenger antigen attached to the well wall do not fluoresce.

Figure 38A:
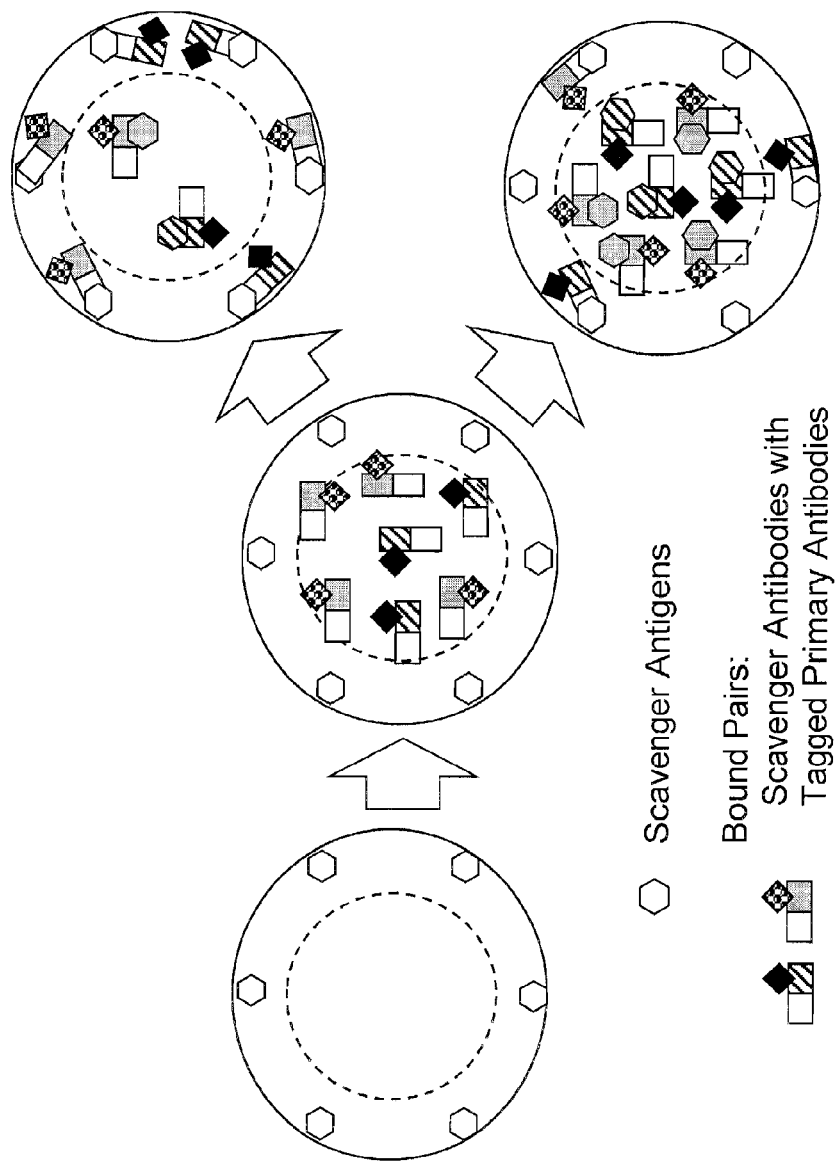
FIG. 38A is a schematic representation of the immunoassay of multiple analytes of the present invention showing the preferred use of multiple distinguishing tags.
Figure 38B:
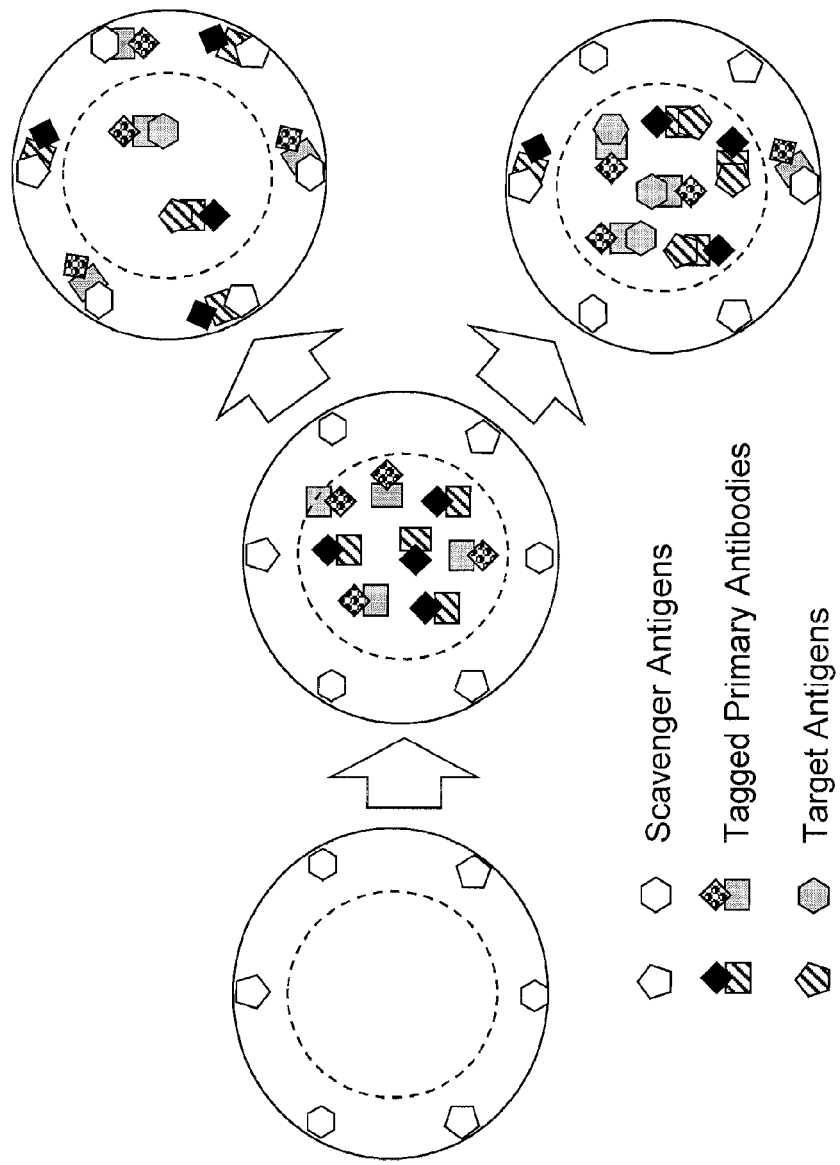
FIG. 38B is a schematic representation of the immunoassay of multiple analytes of the present invention showing the use of more than one type of scavenger antigen and the elimination of the corresponding conjugated scavenger antibodies.

FIG. 38A provides a schematic representation of the immunoassay of multiple analytes of the present invention showing the preferred use of multiple distinguishing tags. FIG. 38B is a schematic representation of the immunoassay of multiple analytes of the present invention showing the use of more than one type of scavenger antigen and the elimination of the corresponding conjugated scavenger antibodies. These and other embodiments of ISAMA include characteristics noted in Table 2.

TABLE 2

Multiple Analytes Methodology Features

| No. | Description of Characteristics of Embodiments |
|---|---|
| 1 | Detection is accomplished with a beam of electromagnetic energy or radiation. The beam is shielded, focused, lased, or controlled in some way so as specifically to avoid illumination of areas where scavenger antigens are located. |
| 2 | Scavenger antigen is obtained or prepared, as is scavenger antibody. The scavenger antibody is conjugated with primary antibody (target antibody) in a ISAMA antibody pair. The scavenger antibody binds to scavenger antigen with a lower binding affinity or avidity than that with which the primary antibody binds to analyte or target. |
| 3 | Scavenger antigen is bound to a portion of the well that is not illuminated by the detection beam but the tagged ISAMA antibody pair-containing test solution yet contacts that portion of the well. |
| 4 | Scavenger antibody and primary antibody (target antibody) are conjugated in such a way that both scavenger antibody and primary antibody cannot or do not bind to their respective goals (i.e., scavenger antigen and target, respectively) at the same time. |
| 5 | The scavenger antigen may be bound to items floating or suspended in the well, but these items have holes, pits, etc., that shadow tagged ISAMA antibody pairs that bind to the scavenger antigen. |

TABLE 2-continued

Multiple Analytes Methodology Features

| No. | Description of Characteristics of Embodiments |
|---|---|
| 6 | Primary antibody (target antibody) is obtained or prepared that binds tightly to the target antigen in order to ensure that ISAMA antibody pairs preferentially bind to targets. |
| 7 | Each different species or kind of target antibody is conjugated with a tag that fluoresces or radiates in a distinguishing way (e.g., at a different wavelength) when struck by the detection beam. The resulting fluorescence or radiation is detected by devices inside or outside the well. |
| 8 | Tagged ISAMA antibody pairs are capable of being dissolved or suspended in the test fluid. |
| 9 | The detection beam can be switched on and off, and yet the signal from the tagged ISAMA antibody pair can be detected during the off periods. |
| 10 | The detection beam can be continuous, and yet signal from the tagged ISAMA antibody pair can be detected as an additional signal. Signal from a well may be separated into individual components (e.g., wavelengths corresponding to signals from different species or kinds of targets) by a photospectrometer or other device (i.e., signal from a well may be analyzed for the identification and quantification of individual species or kinds of targets that are bound by corresponding tagged ISAMA antibody parts). |
| 11 | The detection of the signal from tagged antibodies can be accomplished from a range of angles. |
| 12 | The well has lips that provide additional shadow area to shield the scavenger antigen from the detection beam. |
| 13 | The well has ridges on its walls that provide additional shadow area to shield the scavenger antigen from the detection beam. |
| 14 | The well has depressions or holes that provide additional shadow area to shield the scavenger antigen from the detection beam. |
| 15 | The well bottom does not reflect or scatter the detection beam back into the well. |
| 16 | The test fluid surface may be flat and does not act as a lens. |
| 17 | The test fluid surface may be made flat by contact with a well top. |
| 18 | The test fluid surface may be made flat by avoiding surface tension differences between the fluid and the well. |
| 19 | The test fluid surface may be made flat by filling the well exactly to the neutral fill volume between the meniscus above and below the top of the well. |

Cassette Structures for Testing Fluids and Methods of Use in Immunosorbent Assays In some embodiments, the test cassette includes a plurality of wells with capacity to contain samples and reagent. Ways in which reagent is contained within a well may be used to characterize various embodiments or configurations of the test cassette (for example, as summarized in Table 3).

TABLE 3

Methods for Containment of Reagents

| No. | Containment of Reagent within a Well |
|---|---|
| 1 | Adhered to the wall of the well. |
| 2 | Adhered to sphere(s) or other shape in the well. |
| 3 | Absorbed on a sponge or other absorbent material in the well. |
| 4 | In a liquid in the well. |

A well may be divided into a plurality of compartments. A reagent portion of a well (e.g., a portion corresponding to the well portion in the outer sleeve or back plate of the second embodiment of the cassette) may be isolated from the balance of the well to prevent reagent-sample mixing until mixing is desired.

Well portion volumes may be carefully controlled in order to permit use of the known volume of a well portion for estimating or measuring the volume or amount of a reagent or other liquid sample occupying the well portion. Such estimates or measurements may be helpful in calculating the concentration of a compound (e.g., an analyte in a sample) in a liquid in the well.

Wells may be kept free of sample fluid until desired. Sample may be introduced into wells through capillary action, injection, pouring, suction or other means known to those skilled in the art (e.g., by submersion).

A clear pane may cap a well at one or both ends. If a well has a clear pane at both ends, light may pass completely through the well. Pane surfaces and other well surfaces (or non-surface materials) may be a certain color and allow light of only certain wavelength(s) to reflect from (or pass through) them. In particular, well surface and non-surface materials may be completely transparent and allow light to pass through wells in any direction.

The cassette may have an identifying mark or marks [e.g., bar code, radio frequency identification (WID) tag, detents ("click-stops"), or other marks known to those skilled in the art] that allow a detector to identify a cassette that has been placed in the detector.

The Detector

In some embodiments, the detector simultaneously emits a light consisting of range(s) of wavelengths, i.e., of one or several different spectra. The detector may also emit only one wavelength, or a plurality of different wavelengths, of light over programmed time period(s). Light typically shines into, or through, a well during testing.

In some embodiments, the detector includes a plurality of light receivers. These may capture light that has traveled through reagent, sample or mixtures of reagent and sample. In some embodiments, the detector may include only one light receiver; this receiver may be capable of capturing light reflected from, or transmitted through, one or multiple wells.

A light receiver usually is connected to a device that can process data (e.g., match a colorimetric measurement from a table of potential readings in order to identify, quantify, or both identify and quantify, analyte in a tested fluid).

In some embodiments, the detector includes a man machine interface (MMI) that allows an operator to control the detector as well as to save and download data generated from analysis using the cassette. This MMI may be integral to the detector or be part of a separate computer connected by a direct communication cable or a network link to the detector.

A First Embodiment of the Test Cassette/Detector

In a first embodiment, a cassette has a plurality of (e.g., more than 100) wells. The cassette includes three parts: a generally circular reagent well plate, a central water or sample well plate, and a generally circular cover. Well bottoms of the reagent well plate are opposite the bulk of the rest of the cassette. The wells or well portions of the other two plates transverse or pass through those plates. All three plates are held together tightly at the center, and yet they may be caused to rotate relative to each other about the center (while permitting various wells to remain sealed).

Some wells may be used for calibration purposes (e.g., for comparing transmitted or reflected light values to expected values). In some configurations, the cover and the reagent well plates are made of an optically clear plastic.

After reagents are loaded into reagent wells or reagent well portions, the central water (or sample) well plate may be rotated or affixed relative to the reagent well plate in such a way that the wells or well portions of the two plates do not align.

The cover plate may be rotated or affixed to prevent any water or other sample fluid from entering wells or well portions of the central plate until the cover plate is rotated into a well-alignment position. When the cover has been removed or turned to a position where holes in the cover are aligned with wells or well portions of the central plate, water or other liquid sample can enter and fill wells or well portions of the central plate (i.e., samples can be taken). The cover plate may then be replaced or further turned so that samples are sealed within the wells or well portions.

When a test is to be run, the reagent well plate may be rotated so that wells or well portions of the reagent well plate align with wells or well portions of the central plate. For each aligned well, reagent can then mix with a corresponding sample. Light also then may be allowed to pass through the cover overlying a sample well, through sample of an aligned central plate well portion and through reagent of an aligned reagent plate well portion, even as sample mixes with reagent. If the sample-reagent reaction may be assayed or measured through a colorimetric means, detected and measured light characteristics can then be translated into data (e.g., colorimetric data may be used to calculate analyte concentration in a sample).

In some configurations, the reagent well or reagent well portion is filled nearly to capacity. A small void or gas space may form (i.e., a bubble may form) when a reagent well or reagent well portion is aligned with a sample well or sample well portion. This bubble may provide space to facilitate or permit mixing liquid sample (e.g., a water-dissolved sample) and reagent by agitation.

In some configurations, a well or well portion may be larger in diameter at one end versus another end. If a void or gas space (i.e., a bubble) forms at a larger-diameter end of a well or well portion, the bubble's small size relative to the well diameter may permit light from a detector to pass through the well in a path that does not encounter the bubble.

The detector may emit lights of various wavelengths that pass through a cassette. One device that converts light to an electrical or digital signal (such as a charge coupled device or CCD) may be used to collect light after it has passed through a well or wells of a cassette.

When a cassette is snapped into a detector, the detector reads the barcode, WID tag, or other identifying mark(s) and determines the type(s) of tests that may be executed. The detector then proceeds through a preprogrammed sequence of light emission and capture and data collection steps (e.g., for the collection of colorimetric data). Specialized software is used in the collection and analysis of data. Raw collected data, as well as results from analyzing the collected data, are saved (optionally with date, time, program parameters, etc.). The saved data and results may be reviewed immediately or recalled for review at a later time.

A Second Embodiment of the Test Cassette/Detector

In a second embodiment, a cassette has a plurality of (e.g., more than 100) wells. The cassette includes two major parts: an outer sleeve or back plate and an inner or front plate. Each part preferably includes wells or well portions. In some configurations, well bottoms are clear (well bottoms may be molded during formation of well walls or affixed after well walls are formed).

As in the previously described first embodiment, some wells or well portions may be used for calibration purposes (e.g., for comparing transmitted or reflected light values to expected values).

In some configurations, the outer sleeve or back plate includes reagent wells or reagent well portions and fill channels. The inner or front plate includes wells or well portions for water or other sample liquid(s). In one configuration, wells or well portions of the two plates are not aligned and reagent is sealed (with a small gas bubble) in each well or well portion of the outer sleeve or back plate.

In some configurations, a cassette of the second embodiment includes a third major part: a "trigger" or plunger. This trigger or plunger may be spring loaded. Movement of the trigger seals (or opens) one or more entry ports (e.g., along a side of the cassette) to one or more wells.

When the trigger is depressed in some configurations, ports (e.g., a top port and a bottom port) are opened on the side of the cassette's outer sleeve. These ports may connect to runners or channels that in turn connect to wells or well portions of the front or inner plate. Paths for movement of water (or other liquid sample or displaced air or other gas) between runners or channels of the outer sleeve to wells or well portions of the cassette's s inner or front plate may thus be opened. This provides a path for water or other liquid sample to enter, for example, through the bottom port, continue through runners or channels of the outer sleeve, and fill into wells or well portions of the inner or front plate. In this configuration, displaced air or other gas may leave the cassette through the top port.

When a cassette is filled and the operator is ready to test liquid sample(s), the inner or front plate may be pushed so as to align sections of reagent well or well portions of the outer sleeve or back plate with water or sample wells or well portions in the cassette's inner or front plate. Agitating or shaking the cassette permits reagent and liquid sample to mix (a residual bubble may provide space to facilitate mixing).

As noted for the previously described first embodiment, a detector for use with a cassette of this second embodiment may emit (or capture or both emit and capture) lights of various wavelengths. A detector (or other device) may be used to capture light that has passed through, or reflected from, or passed through and reflected from, one or more wells of this second embodiment.

Water or other liquid sample may be added to wells or well portions of the cassette's inner or front plate in various ways, including: 1) depressing the trigger and injecting sample fluid into wells; or 2) submerging the cassette in water or other liquid sample and then depressing the trigger in order to release air from the wells and to permit water or other sample liquid to fill the wells or well portions of the inner or front plate. Water or other liquid sample may be added to multiple cassettes at the same time but from various depths (e.g., of larger volumes of water or other liquid sample) in order to obtain, for example, a depth profile of the water or other liquid sample.

After the cassette is snapped into the detector, the detector reads the barcode, RFID tag or other identifying mark(s) and determines the type(s) of tests that may be executed. The detector may then proceed through a preprogrammed sequence of light emission(s), light capture(s) and other data extraction and analyses. As noted previously for configurations of the first embodiment, specialized software is used in the collection and analysis of data. Raw collected data, as well as results of collected data analysis, are saved (optionally with date, time, program parameters, etc.). Also as previously noted for configurations of the first embodiment, the saved data and results may be reviewed immediately or recalled for review at a later time.

A Third Embodiment of the Test Cassette/Detector

A third embodiment includes a detector that may contain a magazine of cassettes. The detector (or cassette/detector system) may process cassettes of the magazine serially or as a group (and, in some configurations, with little or no human intervention). The detector could, as pre-programmed, obtain a reading from a sample, analyze it, and then: a) send data to a user, b) store the data for later retrieval, or c) accomplish both. This third embodiment could also be set up so that the system only cycled when a sample was entered into the system.

Figure 14:
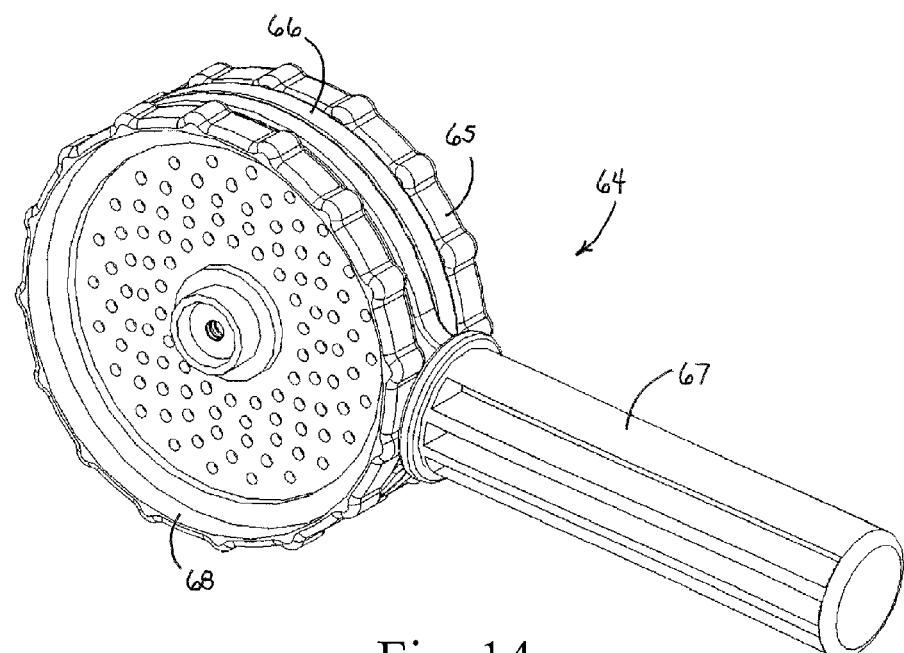
FIG. 14 is a cassette structure for testing fluids.
Figure 15:
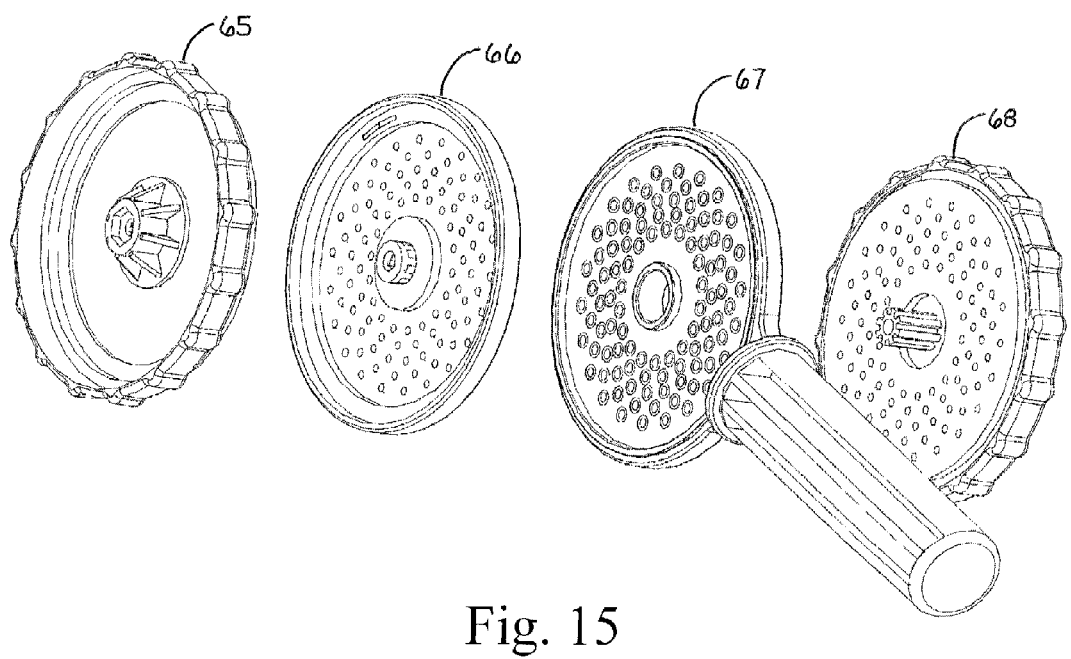
FIG. 15 is a disassembled cassette structure for testing fluids.
Figure 16:
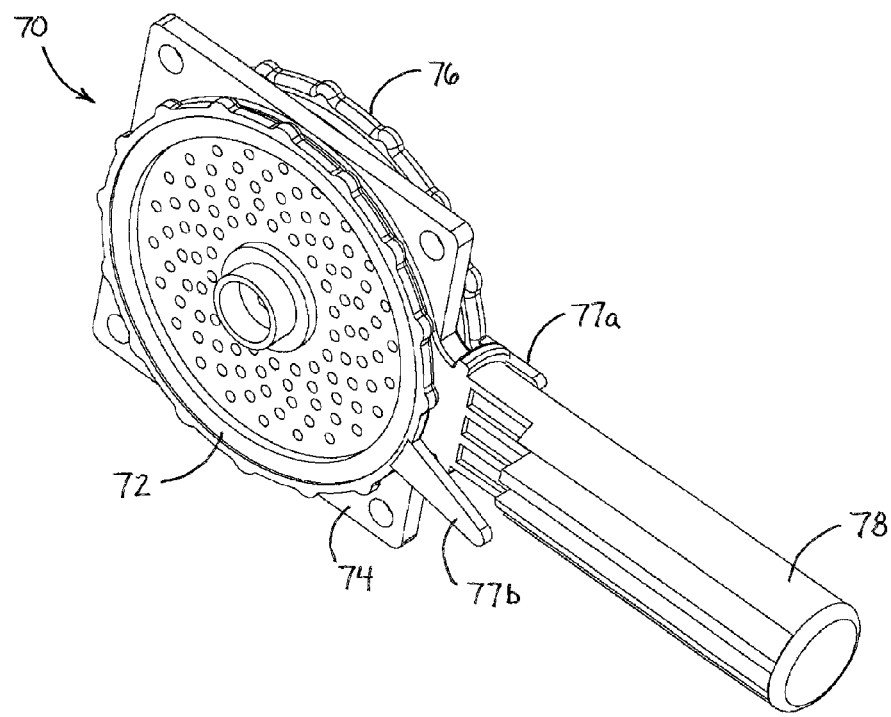
FIG. 16 is an oblique view of a first embodiment of a cassette for testing fluids.
Figure 17:
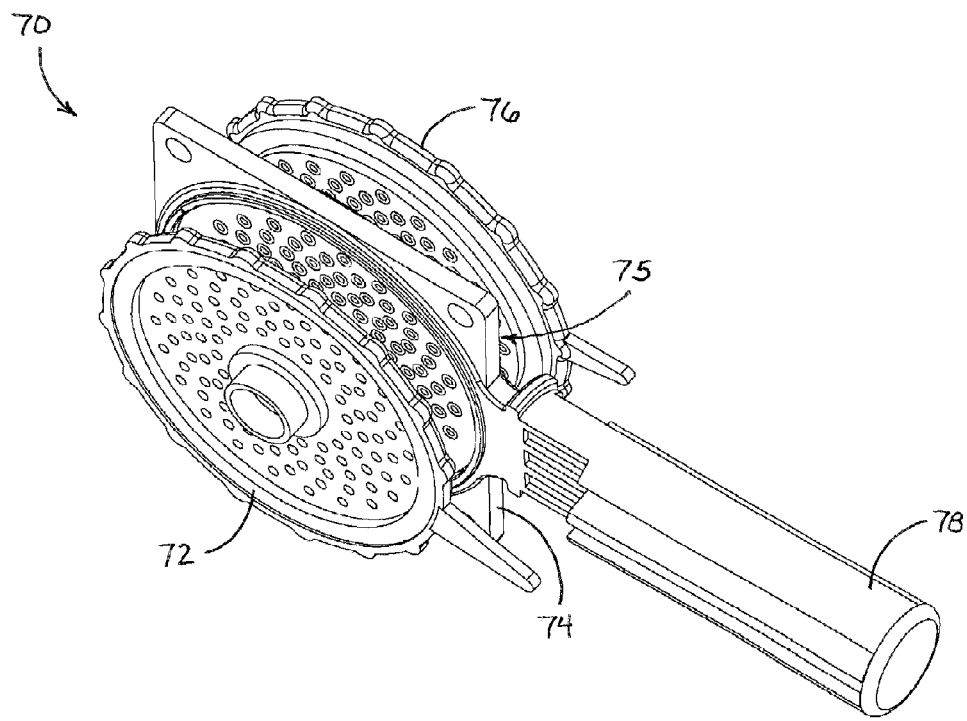
FIG. 17 is an exploded view of this first cassette embodiment such that wells or well portions may be better viewed.
Figure 18:
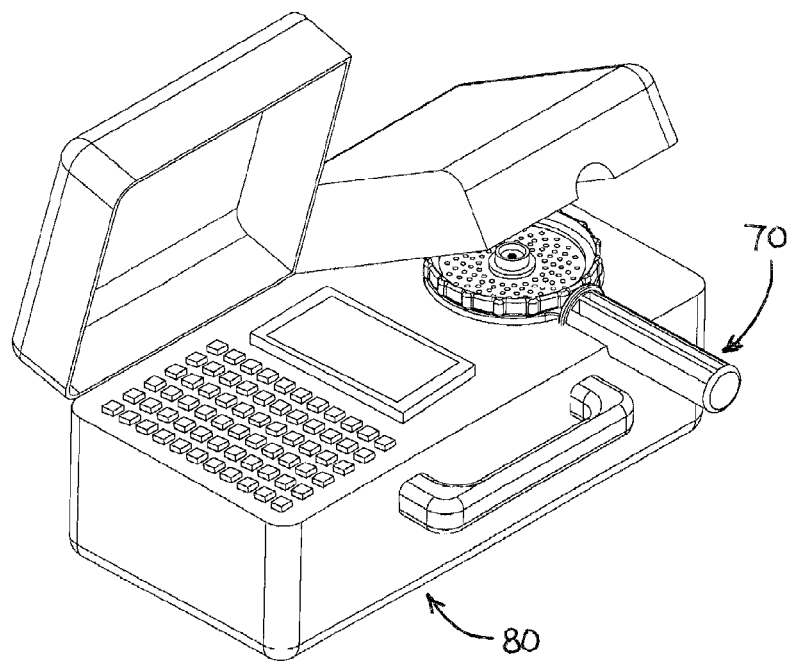
FIG. 18 depicts a cassette similar to this first cassette embodiment in a portable, self-contained detector.
Figure 19:
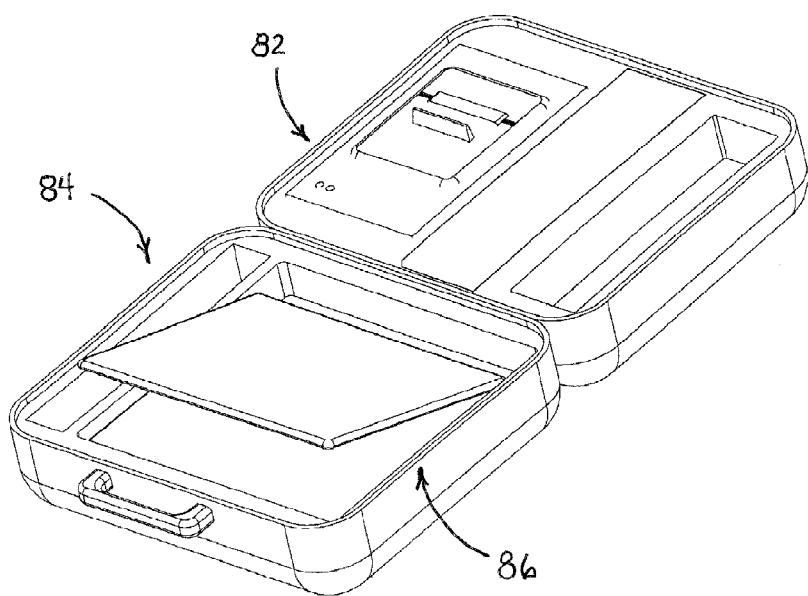
FIG. 19 depicts a simple detector connected to a laptop wherein the detector and laptop are held in a commercial "briefcase;"

FIG. 14 is a cassette structure for testing fluids. FIG. 15 is a disassembled cassette structure for testing fluids. FIG. 16 is an oblique view of a first embodiment of a cassette 70 for testing fluids. The sample wells are in a central plate 74 (generally square with a paddle handle 78). Reagent wells or reagent portions of wells (not visible) are present in a generally circular reagent well plate attached on the far side. A generally circular cover plate 72 is attached on the near side of the central plate 74. This figure also depicts small "handles" 77a and 77b that facilitate rotating the cover plate disk and reagent well plate disk 76. These handles could be alternatively formed as teeth, sprockets, ratchets, etc. FIG. 17 is an exploded view of this first cassette embodiment 70 such that wells or well portions may be better viewed. Circular ridges 75 are depicted around the well circumferences. These ridges are part of seals that isolate the wells or well portions. FIG. 18 depicts a cassette 70 similar to this first cassette embodiment in a portable, self-contained detector 80. FIG. 19 depicts a simple detector 82 connected to a laptop 86 wherein the detector and laptop are held in a commercial "briefcase" 84.

Figure 20:
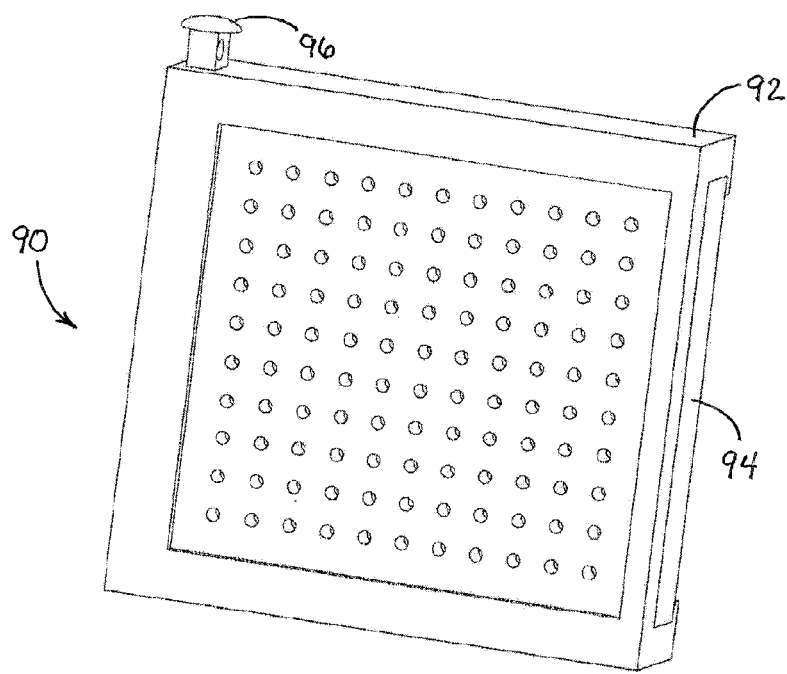
FIG. 20 is a largely broad side view of a second embodiment of a cassette for testing fluids.
Figure 21:
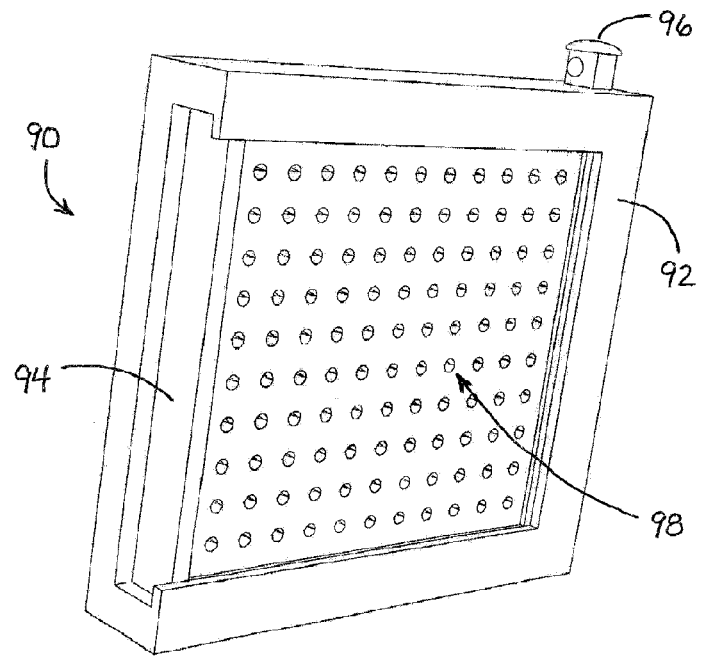
FIG. 21 is an angled side view of this second embodiment depicting sample wells or well portions in an inner or front plate.
Figure 24E:
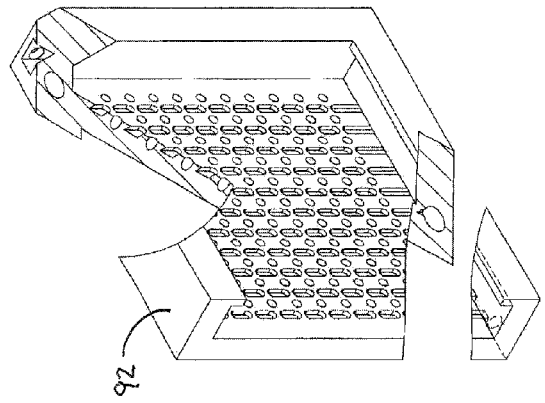
FIGS. 24A-24E diagram further side and cut-away views of an outer sleeve or back plate of this second embodiment of a cassette for testing fluids.
Figure 24B:
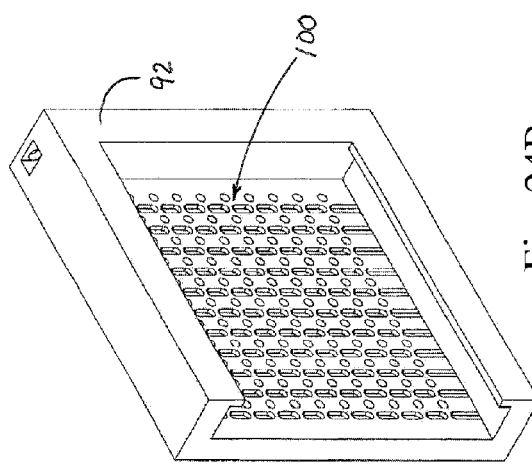
Figure 24D:
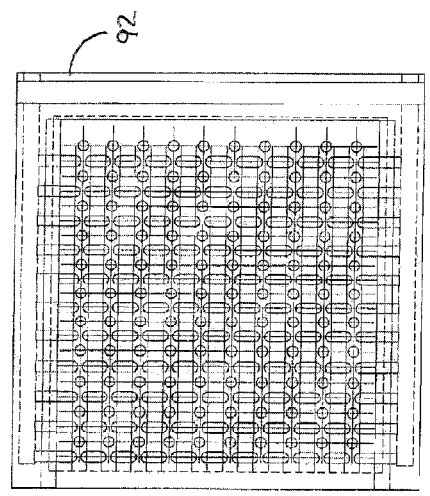
Figure 24A:
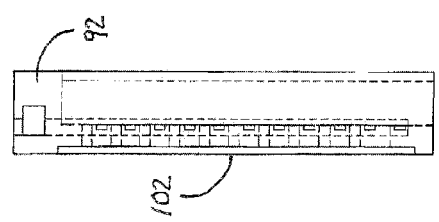
Figure 24C:
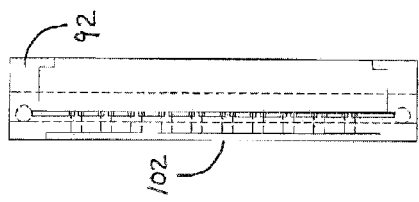
Figure 25E:
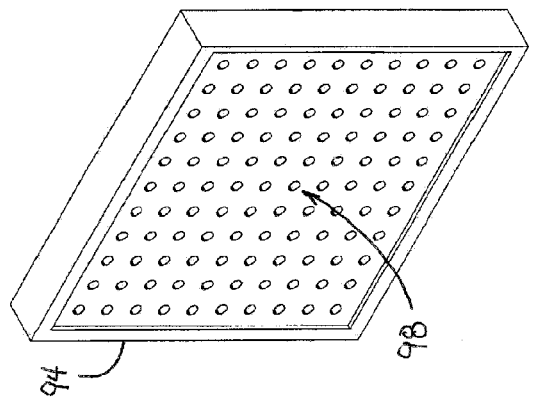
FIGS. 25A-25E diagram side and angle views of an inner or front plate of this second embodiment of a cassette for testing fluids.
Figure 25D:
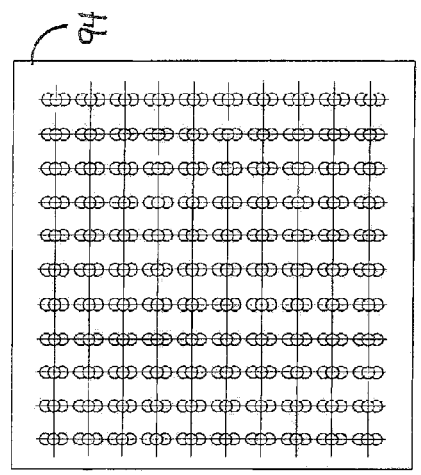
Figure 25C:
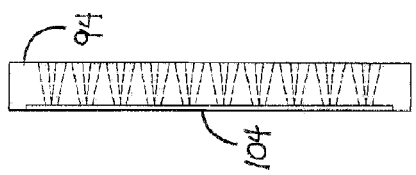
Figure 25A:
Figure 25B:
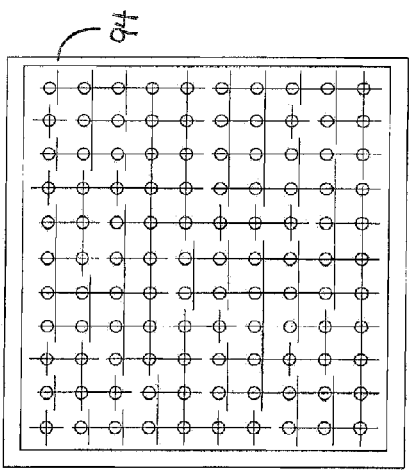
Figure 26D:
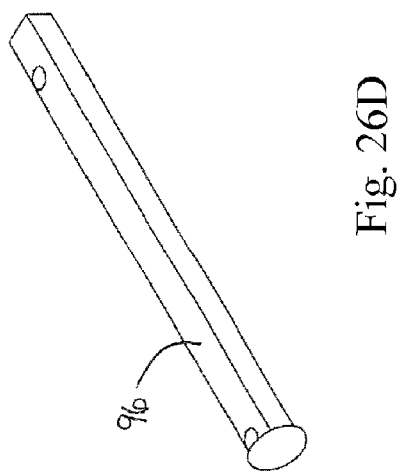
FIGS. 26A-26D diagram a trigger or plunger of this second embodiment of a cassette for testing fluids.
Figure 26C:
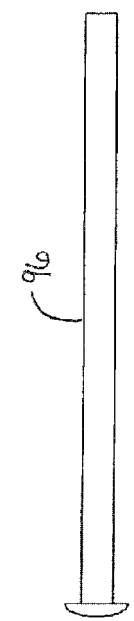
Figure 26A:
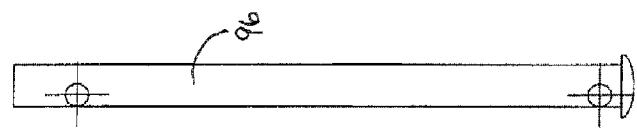
Figure 26B:

FIG. 20 is a largely broad side view of a second embodiment of a cassette 90 for testing fluids having an outer sleeve/back plate 92, an inner/front plate 94, and a trigger/plunger 96. FIG. 21 is an angled side view of this second embodiment depicting sample wells or well portions 98 in an inner or front plate 94. FIG. 22 is a flat-on broad side view of this second embodiment of a cassette 90 for testing fluids. Reagent wells or reagent well portions of wells 100 are visible in the outer sleeve or back plate 92. FIGS. 23A and 23B diagram a diagonal cut-away view of this second embodiment of a cassette 90 for testing fluids.

FIGS. 24A-24E diagram further side and cut-away views of an outer sleeve or back plate 92 of this second embodiment of a cassette 90 for testing fluids. A thin inset 102 covers the outer end of reagent wells or reagent well portions 100 in the narrow side views of the outer sleeve or back plate 92. This inset forms a pane or bottom for reagent wells or reagent well portions in the outer sleeve or back plate.

FIGS. 25A-25E diagram side and angle views of an inner or front plate 94 of this second embodiment of a cassette for testing fluids. Space for a thin inset 104 to cover the wells or well portions for water or sample is diagrammed in the narrow side views, as it is also diagrammed in the front-on, broad side view and the angled view of the inner or front plate. This inset forms a pane or opposite bottom for wells or well portions 98 for water or sample in the inner or front plate. FIGS. 26A-26D diagram a trigger or plunger 96 of this second embodiment of a cassette 90 for testing fluids.

Figure 27:
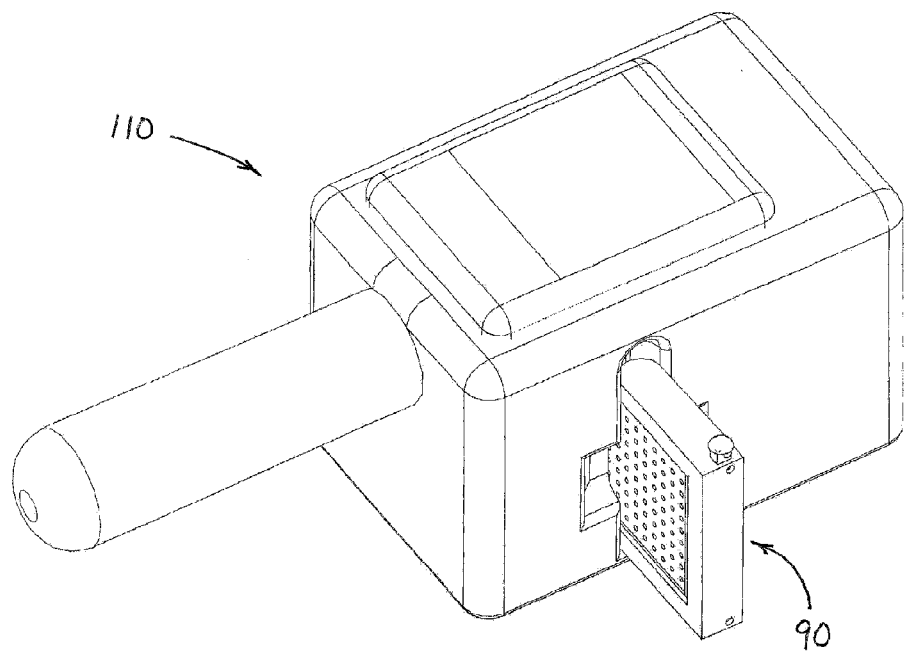
FIG. 27 depicts a detector into which this second embodiment of a cassette for testing fluids is inserted.
Figure 28:
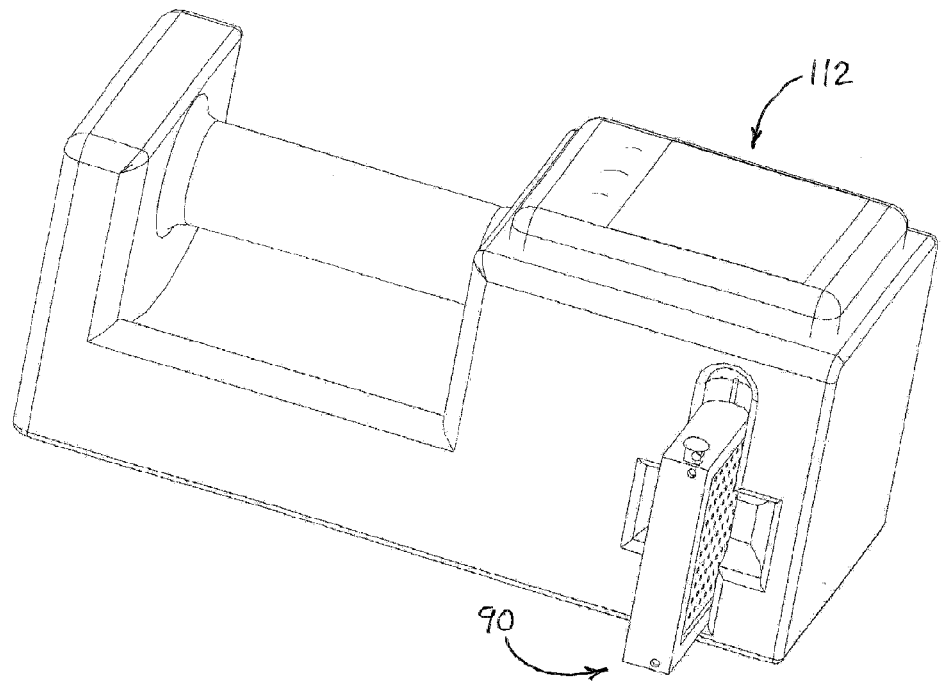
FIG. 28 depicts another embodiment of a detector into which this second embodiment of a cassette for testing fluids is inserted.

FIG. 27 depicts a detector 110 into which this second embodiment of a cassette 90 for testing fluids is inserted. FIG. 28 depicts another embodiment of a detector 112 into which this second embodiment of a cassette 90 for testing fluids is inserted. FIGS. 29A-29C diagram this second embodiment of a cassette 90 for testing fluids in a closed, ready-to-use position. The air outlet port 120 and runner (at the top of the cassette and plunger) are not aligned, and neither is the water or sample inlet port 122 and runner (at the bottom of the cassette and plunger). The cassette is in a sealed, closed, ready to use position. The holes in the front and back pieces are not aligned and the reagent is captured in the back piece. This section view shows the air outlet runner (at top) and the water inlet runner (at bottom) cut off by the plunger 96.

FIGS. 30A-30C diagram this second embodiment of a cassette 90 for testing fluids in a sample-taking position. Both the air outlet port 120 and runner (at the top of the cassette and plunger) and the water or sample inlet port 122 and runner (at the bottom of the cassette and plunger) are aligned. Consequently, water or sample from the cassette's exterior can fill wells in the inner or front plate 94 with water or sample fluid. But the reagent wells or reagent well portions in the outer sleeve or back plate are not aligned with wells or well portions of water or sample in the cassette's inner or front plate.

Consequently, reagent remains captured in the outer sleeve or back plate. The holes in the front and back are not aligned and the reagent remains captured in the back piece. With the plunger 96 depressed, the air outlet runner (at top) and the water inlet runner (at bottom) are now open to the sample media. This allows the sample wells in the front piece to fill with the sample fluid.

FIGS. 31A-31C diagram this second embodiment of a cassette 90 for testing fluids in an analysis position. The trigger or plunger 96 has returned to its original position (again, the air outlet port 120 and runner at the top of the cassette and plunger are not aligned, and neither are the water or sample inlet port 122 and runner at the bottom of the cassette and plunger), and water or sample fluid has been captured in the cassette. When a researcher or an operator is ready to proceed with sample analysis, the researcher or operator may snap or shift the inner or front plate 94 so that the reagent wells or reagent well portions of the outer sleeve or back plate 92 align, or connect, with the wells or well portions of water or sample in the inner or front plate (to the right in this view). This changes the alignment of the wells from the sampling runners to being aligned with the reagent wells. A small bubble left in the reagent wells causes complete mixing when the cassette is shaken (yet stays out of the way in the wide part of the sample well to allow clear detection through the now complete well by the detector).

Figure 32:
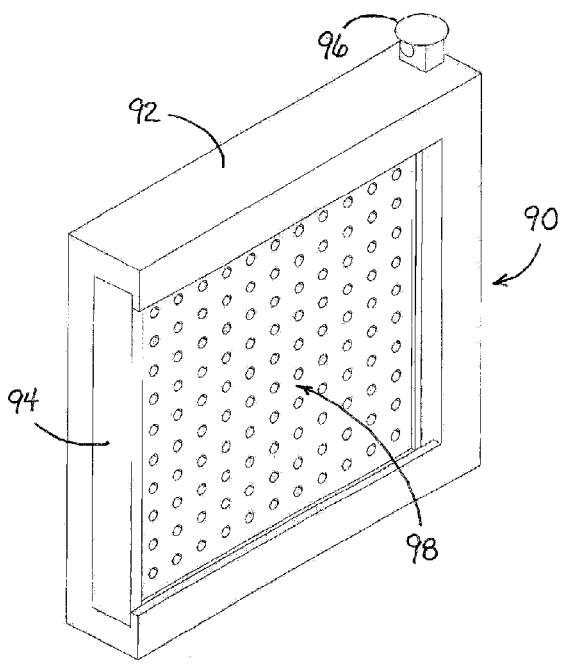
FIG. 32 is another angled side view of this second embodiment of a cassette for testing fluids.
Figure 33:
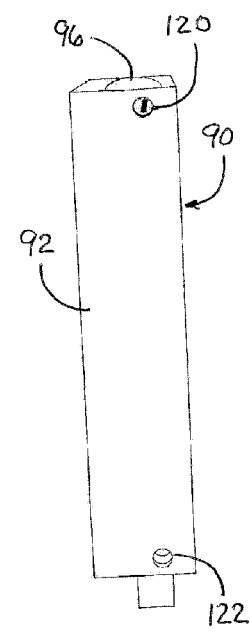
FIG. 33 is a narrow side view of this second embodiment of a cassette for testing fluids. The trigger or plunger is depressed.
Figure 34:
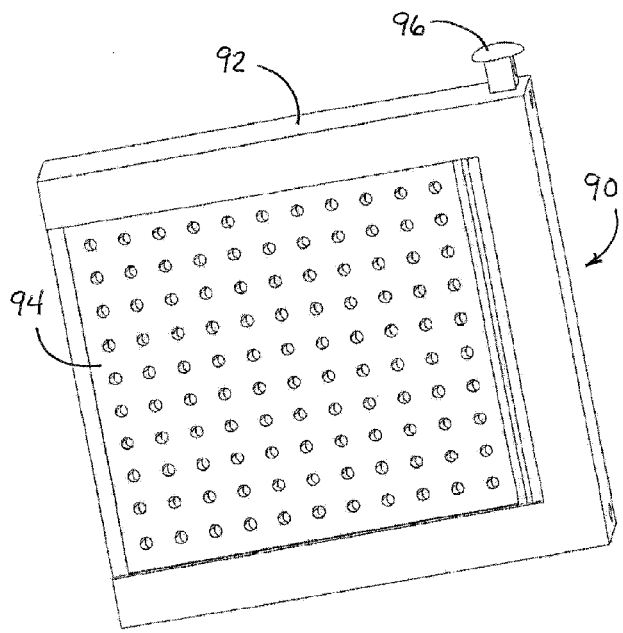
FIG. 34 is a largely broad side view of this second embodiment of a cassette for testing fluids.

FIG. 32 is another angled side view of this second embodiment of a cassette 90 for testing fluids. The trigger or plunger 96 is in its original position. FIG. 33 is a narrow side view of this second embodiment of a cassette 90 for testing fluids. The trigger or plunger 96 is depressed. FIG. 34 is a largely broad side view of this second embodiment of a cassette 90 for testing fluids. The trigger or plunger 96 is in its original position.

Alternate Embodiments of Immunosorbent Assays

The targets for the assays do not need to be suspended in order for the method of the assay of the present invention to be performed. Any reasonably clear fluid may be tested. In this case, fluid includes liquid, gas, or a combination thereof. Water from a river, ocean, or pool may commonly be tested. Body fluids such as urine, saliva, and blood may also be tested. Oils may also be analyzed. However, targets for the assays do not need to be floating. In one preferred embodiment of the method of the present invention, substances which are bound, attached, or part of a surface may be tested as long as the surface can be submerged in a reasonably clear fluid. Surface detection may occur as in the case of a test strip (e.g., metal, wood, or glass) which is put in water.

Any of the methods of the present invention may also be performed with an "indirect assay" which is known in the art. In this case, the antibody with the fluorescent label does not bind directly to the target organism, but to the untagged primary antibody. The untagged primary antibody binds to the target, a tagged antibody binds to the untagged primary antibody. A plurality, if necessary, of scavenger antigens pulls the excess of both the tagged antibody and the untagged primary antibody out of the fluid. The advantages of this embodiment of the assay are more colorimetric choices and lower cost.

There may also be variability in the scavenger antigens which are used. They can be identical to the target, a modified target (chemically, physically, or by adding energy), or a wholly new molecule or molecular surface. The key factor is that the antibody binds no better to the scavenger antigen than to the target antigen. The scavenger antigen may be a chemically altered target antigen or it may be synthetically created.

The tagged antibodies may be tagged in any of a variety of methods known in the art including fluorescent, luminescent, radioactive, magnetic, and enzymatic. The target antigens may be anything for which an antibody may be developed such as various chemicals including pesticides, endocrine disruptors, and toxins. This may of course include drugs, both legal and illegal. The target antigens may also be any microorganism, such as bacteria and viruses.

In the methods of the present invention, the sample volume may be concentrated either before or during the assay by any of a number of traditional methods of concentrating that are known in the art. The sample volume may also be concentrated by a less well known methodology wherein a fluid sample is inserted into a cone-shaped vessel and concentrated in a fiber trap to a single point at the bottom of the cone. The micro-organisms are illuminated by fiber optics and a camera takes a photo of the area at the bottom of the cone where the fluorescence is detected at a focused spot.

The detection volume, which must be known to determine the concentration of the target antigen, may be calculated by one of many methods known in the art. These methods include methods such as: the known volume of the well, the known weight, the calculated volume based on the volume swept by a beam of radiation or light (such as a columnated light shining through the sample), and the calculated volume that passes through a flow device.

Further alternate embodiments may be used for the well in the immunosorbent assays. A single well vessel such as a petri dish, test tube, or truncated cone may be used. The vessel may have ridged walls. The well may be moving in a space as in flow cytometry or it could occur in a temporary space, such as with a peristaltic pump. The vessel may contain many wells, such as a well plate. The vessel may be a multi-part well such as a cassette having three plates which line up wherein the fluid is mixed by assembling the well structure and moving the plates.

Alternatively, the assay may occur in a structure separate from the well. This structure may include a mesh, screen, honey comb, beads, particles, strands, tapes, or tubes. The selection of the most appropriate vessel is influenced by several variables including the fluid characteristics such as viscosity, density, and turbidity; the timing of the assay; economy; and environmental factors.

There are several alternate embodiments of the basic methodology of the present invention, which may be performed in a number of ways. In its simplest form, a single well is used and the scavenger antigens are bound to the well wall and not the bottom of the well. The sample and antibodies are introduced. The fluid is agitated and detection occurs through the middle of the well. Alternately, a split well may be used, such as a cassette, wherein multiple pieces of a well are combined to make a single well for detection. Another method is to use one vessel for mixing the sample and the antibodies and then pouring it into the well (or wells) with the antibodies attached and wherein detection occurs.

Another approach is to use one vessel for mixing the sample and antibodies then adding the scavenger antigens which are bound to a structure and agitating. Then the mixture is poured into the well to detect. Alternatively, the sample and antibodies may be mixed in a vessel and then poured into a second vessel containing scavenger antigens (this vessel could be a tube lined with scavenger antigens). The fluid is poured into a well for detection. Also, the sample and antibodies may be mixed in a vessel and then passed through a conduit, or beads, etc. lined with scavenger antigens and then analyzed in a well.

Also useful, particularly in an automated process, are the methods wherein the sample and antibodies are mixed in one vessel, poured into a second vessel, then scavenger antigens which are bound to a structure are added. The mixture is agitated and then poured into a well for detection.

The wide commercial applicability of the various embodiments disclosed herein extends from conventional laboratory usage to portable devices which are field deployable. These settings include: retail testing kiosks, employer drug testing sites, remote healthcare and development projects, natural disaster relief efforts, and war zones. Some of these embodiments would be submersible. Others would be utilized for in-line flow projects such as municipal water district and pool water industry analysis. Some of these designs may be utilized for the analysis of gases and vapors as well as liquids.

Continuous Immunosorbent Assay

A separate method which allows continuous analysis for single or multiple analyte may be performed, wherein no specific well is utilized and the sample is continuously flowing and mixed with antibody. In this method, a structure having bound scavenger antigens attached to it moves continuously through the mixed sample. As the mixture continuously flows through the system, excess antibody is removed from the mixture and the sample is analyzed. This method is particularly useful for analysis of water supplies for municipalities and public pools.

Key elements of this methodology include a mechanism which permits the continuous flow of the target, the flow and regeneration of the antibodies, and a structure which includes a regenerating surface area for scavenger antigens. In this dynamic methodology, many of the elements utilized in the static methodology are equally applicable, such as the types of samples, the types of scavenger antigens, and the various structures having bound to scavenger antigens.

Figure 35:
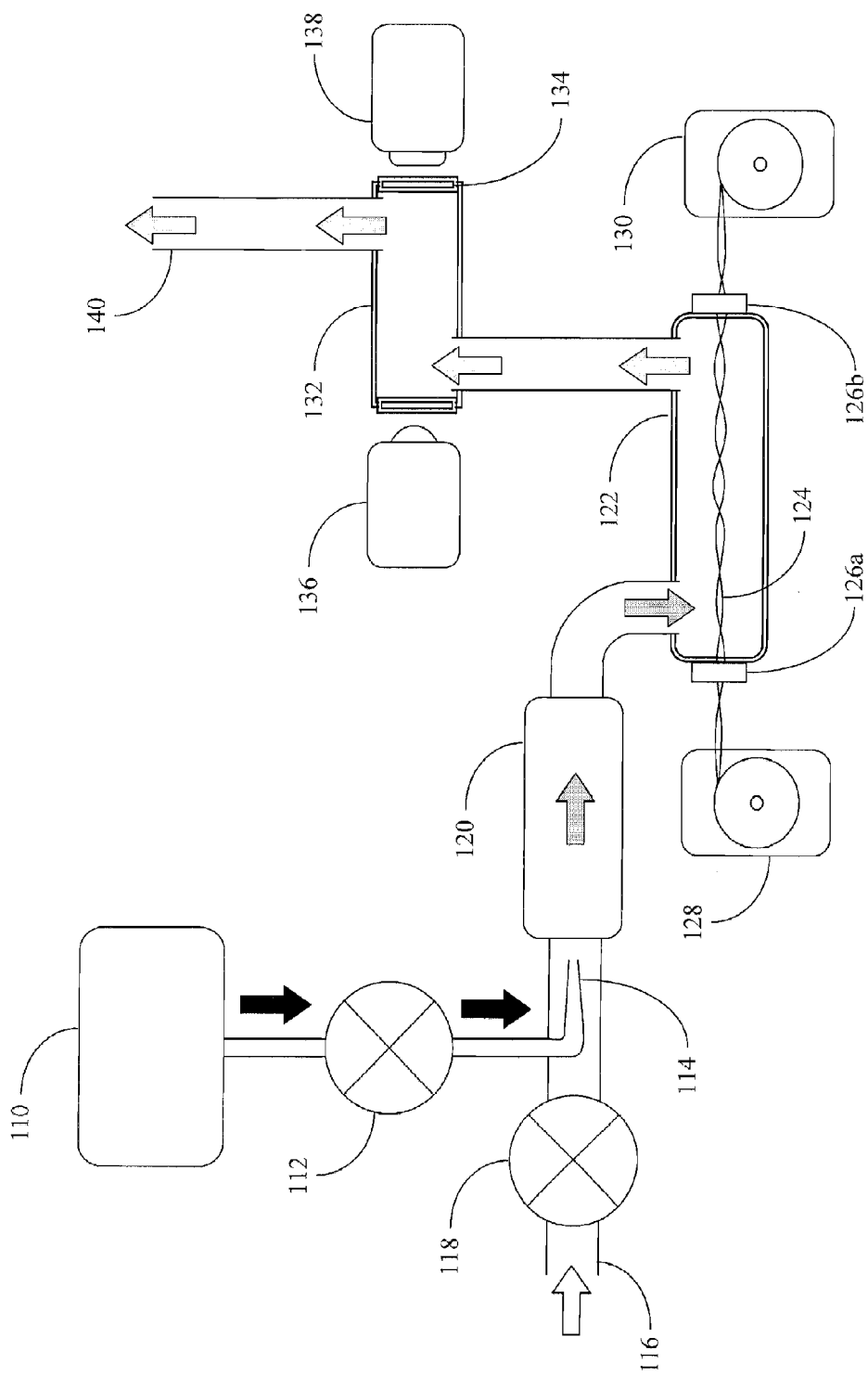
FIG. 35 is a diagram of an embodiment of the continuous flow methodology of the present invention.

As shown in FIG. 35, the methodology for the Continuous ISA extends the ISA to be able to test continuously rather than for only a single test or batch. Instead of admitting a certain amount of fluid to be tested into a vessel and then sealing the vessel, the Continuous ISA operates with the fluid to be tested being pumped on a continuous basis into the device. In this case, the precision of the test is directly related to the precision of the pumps.

The test fluid 116 is pumped into the system with Sample Pump 118. The Tagged Antibody (one or more types) carried in an "inert" fluid is carried from the reservoir 110 and is introduced by the Antibody Pump 112 via flow injection nozzle 114. They are thoroughly mixed in a mixing chamber 120 (the preferred method is with a static mixer well known in the art). The mixing chamber must be sized to provide sufficient mixing based on the flow rates. Once the combined fluid passes through the mixing chamber where the targets have come into contact with the tagged antibodies, the fluid passes through the scavenging chamber 122.

The scavenging chamber is where the fluid comes into contact with the scavenger antibody to remove the excess antibodies. If the test is for a short period, the scavenger chamber may be fixed and have enough scavenger antibody affixed to the walls, beds, screens, etc. to capture all of the target antibody for the test. The preferred method is to have the scavenger antibody continuously refreshed, so the testing may be done without interruption indefinitely. This may be done by many means (alternating chambers, rotating drum, etc.).

The preferred embodiment uses a tape 124 coated with scavenger antigens. If conjugated pairs of scavenger antibodies and primary antibodies are being provided in the flow from the mixing chamber, then only one type of scavenger antigen needs to be provided on the tape. If conjugated pairs are not being utilized, then multiple types of scavenger antigens must be provided. The tape is fed through the scavenging chamber 122 (in the opposite direction from the test fluid flow) at a rate calculated to be sufficient to capture all the antibodies. The scavenger tape 124 passes from a tape supply reel 130 through seal 126b through the scavenging chamber 122 and through seal 126a to the tape take-up reel 128. The seals prevent the test fluid from leaking out of the scavenging chamber. Between the entry point and the exit point the tape twists to induce turbulence and ensures all of the excess antibodies are removed. The test fluid then flows through a precision detection chamber 132 with optically clear lenses 134 at each end where the fluid is illuminated (via illumination source 136) and evaluated (by photo detector 138) just as in the ISA. The test fluid then flows out of the system through outlet/drain 140. This method may also be used for continuous reagent tests. In this embodiment, the antibody pump would pump in the reagent and the scavenging chamber is not required.

Use of ISAMA for Analysis of Micro-Organisms

Figure 39A:
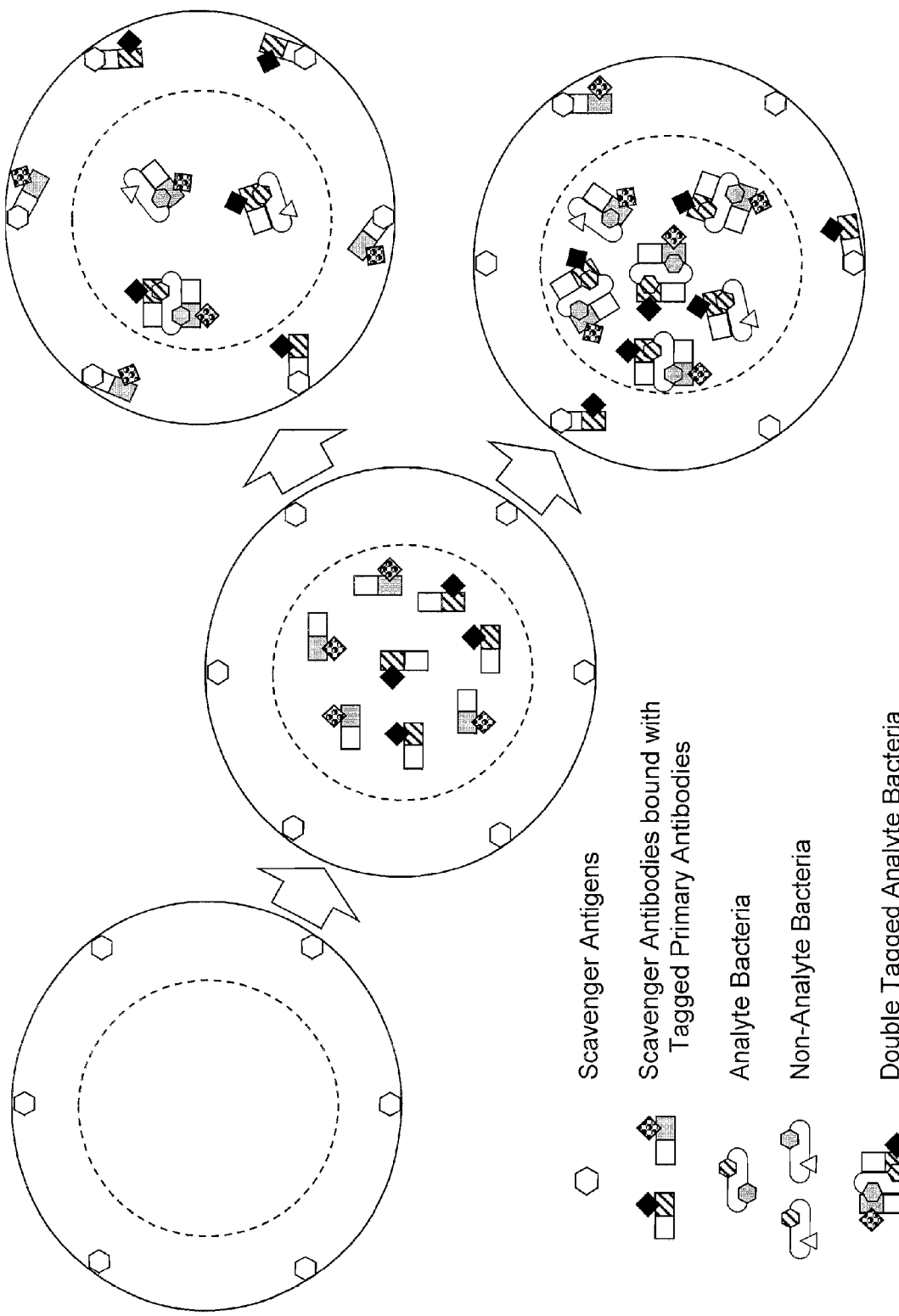
FIG. 39A is a schematic representation of the immunoassay for analysis of micro-organisms of the present invention showing the preferred use of multiple distinguishing tags.
Figure 39B:
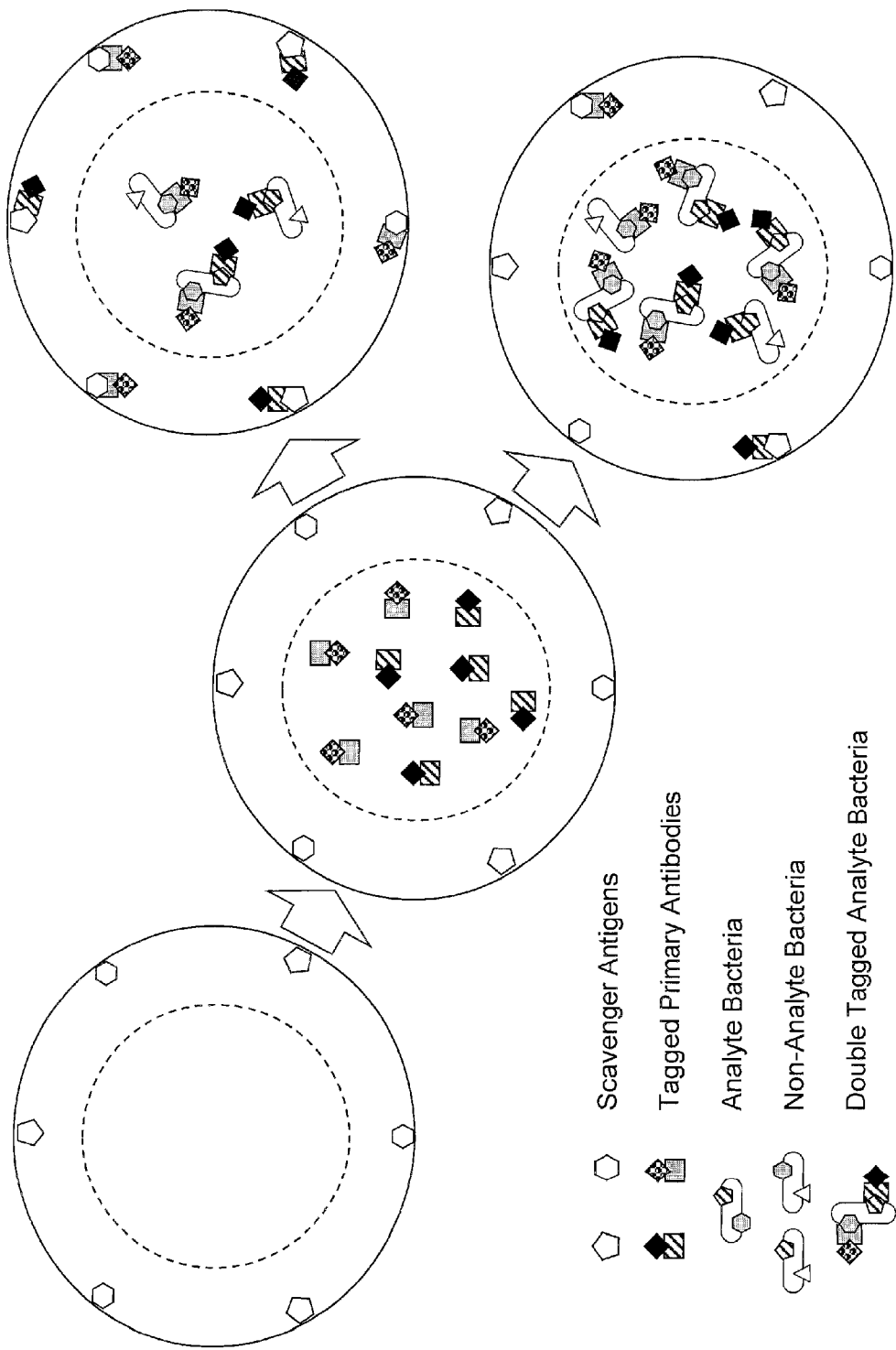
FIG. 39B is a schematic representation of the immunoassay for analysis of micro-organisms of the present invention showing the use of more than one type of scavenger antigen and the elimination of the corresponding conjugated scavenger antibodies.

The various embodiments of ISAMA of the present invention may also be utilized to analyze two different aspects of a single organism or complex molecule (as opposed to one aspect of each of two different species). FIG. 39A and FIG. 39B are schematic representations of the immunoassay for analysis of micro-organisms of the present invention. FIG. 39A illustrates the preferred use of multiple distinguishing tags. In this embodiment, the scavenger antibodies are bound with tagged primary antibodies. The scavenger antibodies of those conjugated pairs that do not bind to analyte bacteria bind to the scavenger antigens. Alternatively, as shown in FIG. 39B, two (or more) types of scavenger antigens may be utilized with the elimination of the corresponding conjugated scavenger antibodies (bound with tagged primary antibodies in FIG. 39A). In this embodiment, the tagged primary antibodies (each having distinguishable tags) bind to a distinct scavenger antigen.

For example, bacteria have various proteins expressed on their surface, including two important types: somatic and flagella. These are commonly referred to by a letter/number designation. For example, in *E. coli* serotype O157:H7, the "O" refers to the somatic antigen (protein) number and the "H" refers to the flagella (protein) number. Together they define a serotype which is a group of microorganisms, viruses, or cells classified together based on their cell surface antigens. Such epidemiologic classification of organisms by serotype is important in determining species and sub-species, pathogenicity, etc.

There are currently no single tests that can identify one serotype. There are ELISA tests that have two sets of antibody steps that can be used to identify serotype. The ISAMA methodology of the present invention can be used with one antibody for the somatic antigen and one antibody for the flagella antigen. Thus by locating the bacteria that glow with both colors, bacteria of that specific serotype can be identified. Bacteria of another serotype may glow in one or the other color, but not with both. Such a test would be very useful for identification of specific types of bacteria, particularly in the field.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth herein.

We claim:

1. An apparatus for immunologically analyzing a sample for at least one analyte, the apparatus comprising:
    at least one well comprising structural elements defining an internal volume, structural elements defining a well wall surface area, and structural elements defining a detection aperture, the well wall surface area obscured from view through the detection aperture;
    a plurality of scavenger antigens bound to the well wall surface area structural elements of the at least one well;
    at least one test fluid comprising a plurality of tagged antibodies;
    means for introducing the plurality of tagged antibodies into the at least one well;
    at least one sample fluid comprising a plurality of target antigens;
    means for introducing the plurality of target antigens into the at least one well to form a combined solution with the plurality of tagged antibodies;
    means for retaining the combined solution of the plurality of target antigens and the plurality of tagged antibodies within the internal volume of the at least one well; and
    means for detecting tagged antibodies bound to target antigens suspended in the internal well volume through the detection aperture.

2. The apparatus of claim 1, wherein the at least one well each comprises first and second well sections, each first well section defining a first portion of the internal well volume and each second well section defining a second portion of the internal well volume and the well wall surface area, and further wherein the plurality of target antigens are contained within the second portion of the internal well volume and the tagged antibodies are introduced into the internal volume of the first well section.

3. The apparatus of claim 2, wherein the first well section is configured within a reagent well plate having a plurality of first well sections arranged in a regular array and the second well section is configured within a sample well plate having a plurality of second well sections arranged in a regular array, the sample well plate arranged in parallel adjacent to the reagent well plate, wherein the first well sections in the reagent well plate may be alternately aligned or misaligned with the second well sections in the sample well plate.

4. The apparatus of claim 3, wherein the means for introducing the plurality of target antigens into the at least one well comprises a means for sliding the reagent well plate laterally with respect to the sample well plate so as to align the first well sections with the second well sections.

5. The apparatus of claim 3, wherein the means for introducing the plurality of target antigens into the at least one well comprises a means for rotating the reagent well plate about an axis with respect to the sample well plate so as to align the first well sections with the second well sections.

6. The apparatus of claim 2, further comprising a cover defining at least one opening, the cover positioned adjacent the second well section wherein the at least one opening in the cover may be alternately aligned or misaligned with the second well section.

7. The apparatus of claim 1, wherein the means for detecting tagged antibodies bound to target antigens suspended in the internal well volume comprises a detector light source and a light sensor wherein the detector light source directs a beam of light through the internal well volume to the light sensor.

8. The apparatus of claim 7, wherein the well wall surface area structural elements are positioned apart from a path of the beam of light.

9. The apparatus of claim 5, wherein the reagent well plate and the sample well plate are positioned in a rotational test cassette, wherein the plurality of first well sections on the reagent well plate are arranged in a radial array and the plurality of second well sections on the sample well plate are arranged in a corresponding radial array, and the reagent well plate is rotationally fixed to the sample well plate at a center point of the radial array.

10. The apparatus of claim 9, further comprising a cover defining a plurality of openings wherein the plurality of openings are arranged in a corresponding radial array, the cover positioned adjacent the sample well plate wherein the plurality of openings in the cover may be alternately aligned or misaligned with the plurality of second well sections within the sample well plate.

11. The apparatus of claim 4, wherein the reagent well plate and the sample well plate are positioned in a rectangular test cassette, wherein the plurality of first well sections on the reagent well plate are arranged in a rectangular array and the plurality of second well sections on the sample well plate are arranged in a corresponding rectangular array, and the reagent well plate is slidingly fixed to the sample well plate with a frame.

12. The apparatus of claim 11, further comprising means for introducing the plurality of target antigens into the plurality of second well sections.

13. The apparatus of claim 12, wherein the means for introducing the plurality of target antigens into the plurality of second well sections comprises a channel array providing a fluid conduit from the inlet through each of the plurality of second well sections in the sample well plate to the outlet.

14. The apparatus of claim 13, further comprising a plunger for alternately opening and closing the inlet and outlet of the channel array.

15. The apparatus of claim 9, wherein the means for detecting tagged antibodies bound to target antigens suspended in the internal well volume comprises a detector light source and a light sensor wherein the detector light source directs a beam of light through the internal well volume to the light sensor, the detector light source and light sensor configured within a portable self-contained case structured to receive the rotational test cassette.

16. The apparatus of claim 11, wherein the means for detecting tagged antibodies bound to target antigens suspended in the internal well volume comprises a detector light source and a light sensor wherein the detector light source directs a beam of light through the internal well volume to the light sensor, the detector light source and light sensor configured within a portable self-contained case structured to receive the rectangular test cassette.

* * * * *